United States Patent
Kuliopulos et al.

(10) Patent No.: US 10,913,781 B2
(45) Date of Patent: Feb. 9, 2021

(54) PEPDUCIN DESIGN AND USE

(75) Inventors: Athan Kuliopulos, Boston, MA (US); Lidija Covic, Boston, MA (US)

(73) Assignee: Tufts Medical Center, Inc., Boston, MA (US)

( * ) Notice: Subject to any disclaimer, the term of this patent is extended or adjusted under 35 U.S.C. 154(b) by 0 days.

(21) Appl. No.: 14/009,479

(22) PCT Filed: Apr. 9, 2012

(86) PCT No.: PCT/US2012/032824
§ 371 (c)(1),
(2), (4) Date: Dec. 9, 2013

(87) PCT Pub. No.: WO2012/139137
PCT Pub. Date: Oct. 11, 2012

(65) Prior Publication Data
US 2014/0087993 A1 Mar. 27, 2014

Related U.S. Application Data

(60) Provisional application No. 61/473,675, filed on Apr. 8, 2011.

(51) Int. Cl.
*C07K 14/705* (2006.01)
*A61K 38/00* (2006.01)

(52) U.S. Cl.
CPC ............ *C07K 14/705* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,464,975 B2 | 10/2002 | Millis | |
| 6,503,511 B1 | 1/2003 | Wizemann et al. | |
| 6,562,958 B1 | 5/2003 | Breton et al. | |
| 6,703,491 B1 | 3/2004 | Homburger et al. | |
| 6,747,137 B1 | 6/2004 | Weinstock et al. | |
| 6,773,893 B1 | 8/2004 | Tall | |
| 6,815,200 B1 | 11/2004 | Krasnykh et al. | |
| 6,864,229 B2 | 3/2005 | Kuliopulos et al. | |
| 7,189,691 B2 | 3/2007 | Hemenway | |
| 7,214,786 B2 | 5/2007 | Kovalic et al. | |
| 7,319,142 B1 | 1/2008 | Goldman et al. | |
| 7,368,531 B2 | 5/2008 | Rosen et al. | |
| 7,527,933 B2 | 5/2009 | Sahin et al. | |
| 7,683,031 B2 | 3/2010 | Ben-Sasson et al. | |
| 7,696,168 B2 | 4/2010 | Kuliopulos et al. | |
| 7,718,762 B2 | 5/2010 | Coggin, Jr. et al. | |
| 7,739,055 B2 | 6/2010 | Stephanopoulos et al. | |
| 7,834,146 B2 | 11/2010 | Kovalic et al. | |
| 7,862,826 B2 | 1/2011 | Murphy et al. | |
| 7,972,993 B2 | 7/2011 | Slootstra et al. | |
| 8,067,671 B2 | 11/2011 | Boukharov et al. | |
| 8,071,732 B2 | 12/2011 | Gaiger et al. | |
| 8,303,962 B2 | 11/2012 | Eckert et al. | |
| 8,389,679 B2 | 3/2013 | Eckert et al. | |
| 8,440,627 B2 | 5/2013 | Kuliopulos et al. | |
| 8,501,930 B2 | 8/2013 | Rozema et al. | |
| 8,575,070 B2 | 11/2013 | Watt et al. | |
| 8,586,006 B2 | 11/2013 | Hood et al. | |
| 8,697,349 B2 | 4/2014 | Hoshino et al. | |
| 9,012,723 B2 | 4/2015 | Guo et al. | |
| 9,029,636 B2 | 5/2015 | Wu et al. | |
| 9,056,905 B2 | 6/2015 | Olson et al. | |
| 9,096,646 B2 | 8/2015 | McMurry et al. | |
| 9,266,930 B1 | 2/2016 | Sette et al. | |
| 9,464,124 B2 | 10/2016 | Bancel et al. | |
| 2003/0088057 A1* | 5/2003 | Traugh ..................... | C07K 7/06 530/329 |
| 2003/0148449 A1 | 8/2003 | Kuliopulos et al. | |
| 2006/0166274 A1 | 7/2006 | Kuliopulos et al. | |
| 2007/0179090 A1 | 8/2007 | Kuliopulos et al. | |
| 2008/0214451 A1 | 9/2008 | Kuliopulos et al. | |
| 2008/0234183 A1 | 9/2008 | Hallbrink et al. | |
| 2009/0270322 A1 | 10/2009 | Kuliopulos et al. | |
| 2010/0137207 A1 | 6/2010 | Kuliopulos et al. | |
| 2012/0028888 A1 | 2/2012 | Janz et al. | |
| 2014/0087993 A1 | 3/2014 | Kuliopulos et al. | |
| 2014/0227718 A1 | 8/2014 | Kuliopulos et al. | |

FOREIGN PATENT DOCUMENTS

| WO | WO-98/16552 A1 | 4/1998 |
|---|---|---|
| WO | WO 01/081408 | 11/2001 |
| WO | WO2004-067712 | * 8/2004 |

OTHER PUBLICATIONS

Kjelsberg et al. (Constituative Activation of the α1b-Adrenergic Receptor by All Amino Acid Substitutions at a Single Site; The Journal of Biological Chemistry; vol. 267 (3) 1430-1433(1992)).*
Kaneider et al. (Nature Medicine Letters; vol. 11 (6); Jun. 2005).*
English Language Translation from Chinese of CN1342658A, publised Apr. 3, 2002.*
Werle et al. ("Strategies to improve plasma half life time of peptide and protein drugs" Amino acids 2006 30:351-367).*
BioNexus (https://www.bionexus.net/category/Peptide+Synthesis.html, available Jun. 7, 2007).*
GenBank: AAU27347 (Science 305; 5692; 1966-1968, submitted Aug. 16, 2004).*
Gether et al., "G Protein-coupled Receptors", The Journal of Biological Chemistry, Jul. 17, 1998, vol. 273, No. 29, 17979-17982.
Covic et al., "Activation and inhibition of G protein-coupled receptors by cell-penetrating membrane-tethered peptides", PNAS, Jan. 22, 2002, vol. 99, No. 2, 643-648.

(Continued)

*Primary Examiner* — James H Alstrum-Acevedo
*Assistant Examiner* — Tara L Martinez
(74) *Attorney, Agent, or Firm* — Clark & Elbing LLP; Susan M. Michaud

(57) ABSTRACT

Disclosed here is the rational design and use of potent and specific GPCR antagonist pepducins based on GPCR regions such as the third intracellular loop and adjacent regions.

12 Claims, 17 Drawing Sheets

Specification includes a Sequence Listing.

(56) References Cited

OTHER PUBLICATIONS

Frateschi et al., "PAR2 absence completely rescues inflammation and ichthyosis caused by altered CAP1/Prss8 expression in mouse skin", Nature Communications, Jan. 18, 2011, 2:161, 1-11 (www.nature.com/.

Extended European Search Report dated May 4, 2018 for European Application No. 17199261.3, Kulipulos et al., "Pepducin Design and Use," filed Apr. 9, 2012 (12 pages).

Kanke et al., "Novel antagonists for proteinase-activated receptor 2: inhibition of cellular and vascular responses in vitro and in vivo," Br J Pharmacol. 158(1):361-71 (2009).

Kelso et al., "Therapeutic promise of proteinase-activated receptor-2 antagonism in joint inflammation," J Pharmacol Exp Ther. 316(3):1017-24 (2006).

Michael et al., "Pharmacological inhibition of PAR2 with the pepducin P2pal-18S protects mice against acute experimental biliary pancreatitis," Am J Physiol Gastrointest Liver Physiol. 304(5):G516-26 (2013).

Sevigny et al., "Interdicting protease-activated receptor-2-driven inflammation with cell-penetrating pepducins," Proc Natl Acad Sci U.S.A. 108(20):8491-6 (2011).

Tressel et al., Chapter 19: Pharmacology, Biodistribution, and Efficacy of GPCR-Based Pepducins in Disease Models, *Cell-Penetrating Peptides: Methods and Protocols*. ed. Langel, Humana Press, pp. 259-275 (2011).

\* cited by examiner

Figure 1F
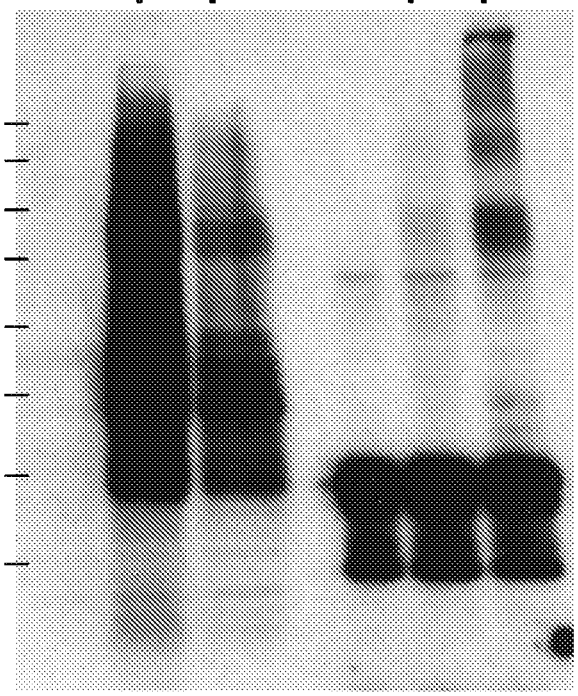
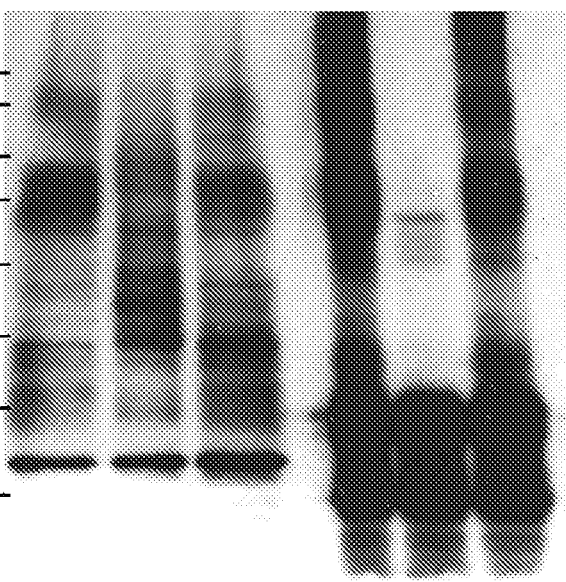

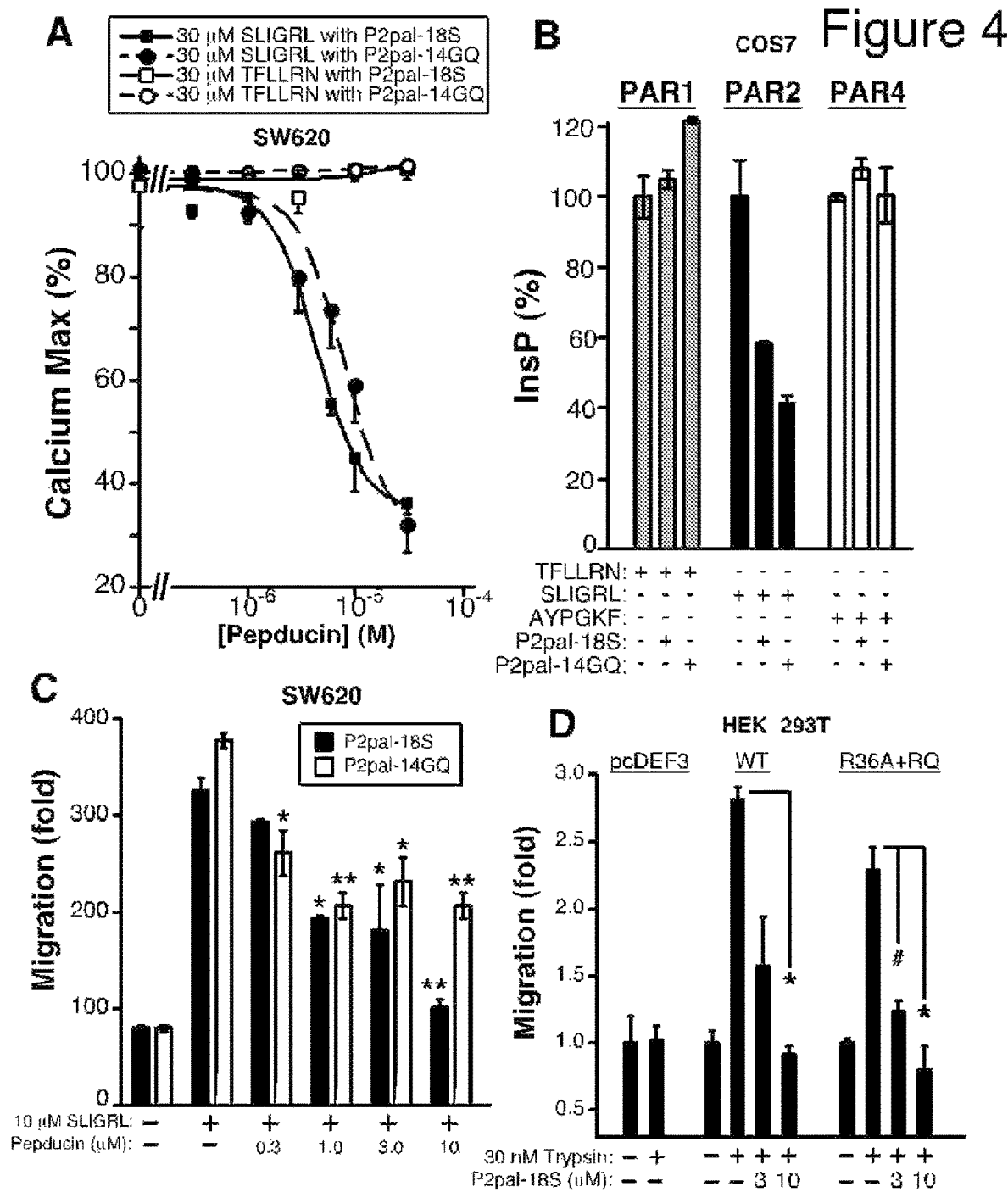

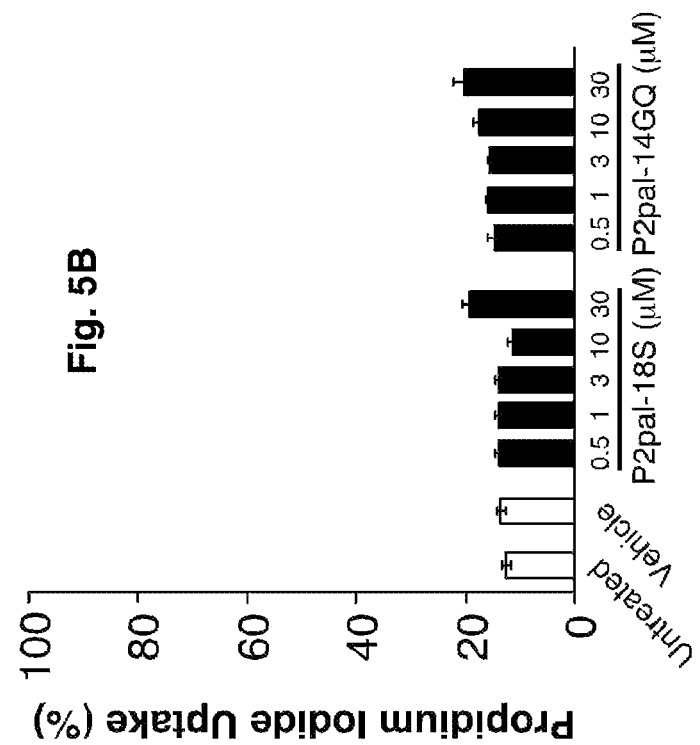
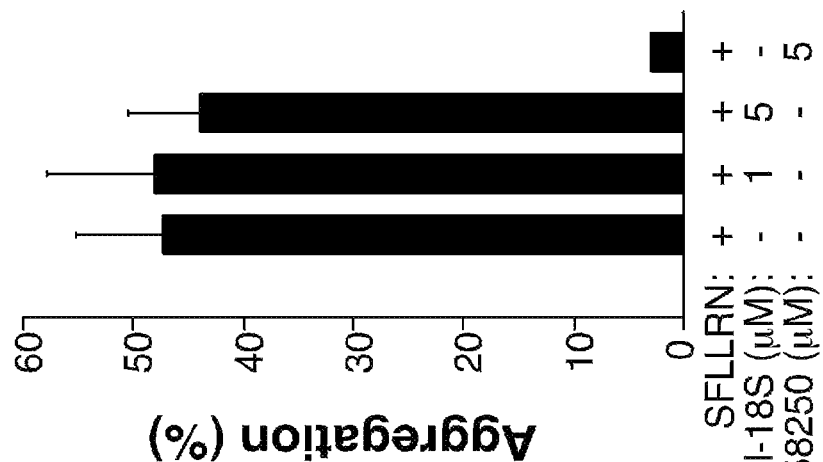
Fig. 5A
Fig. 5B

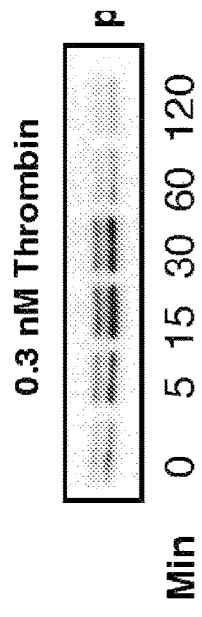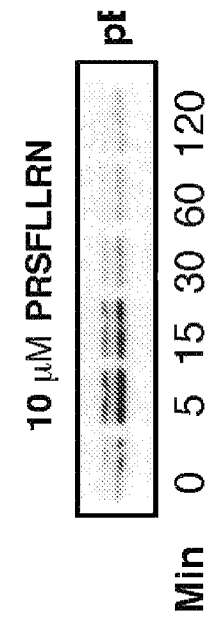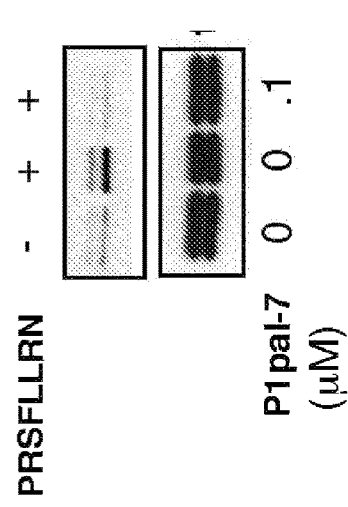
Figure 10

Figure 13
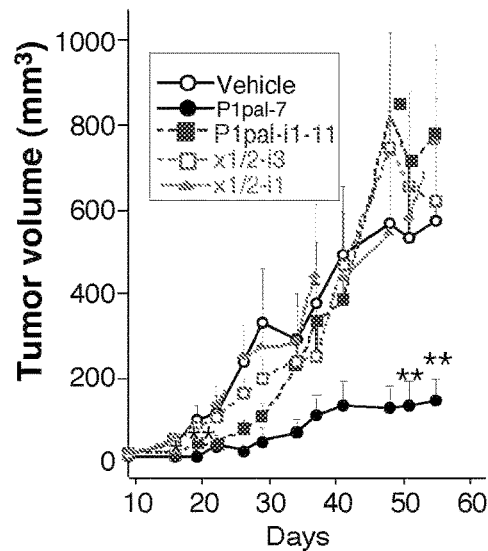
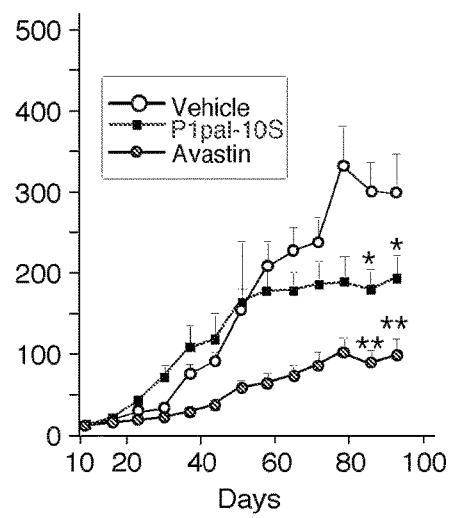
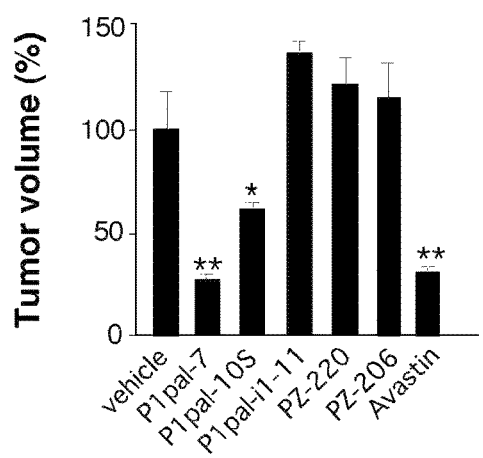
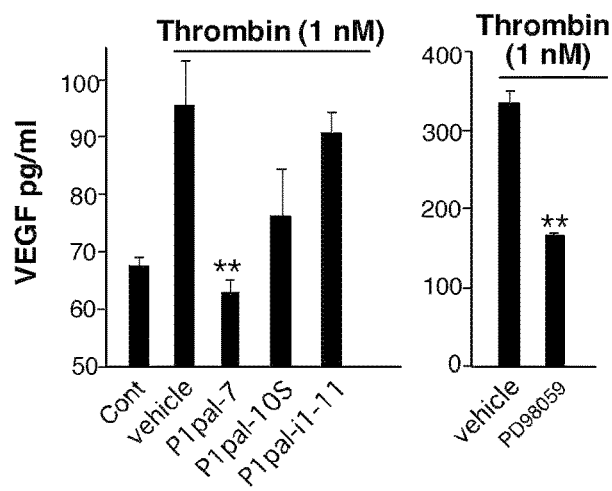

Figure 14
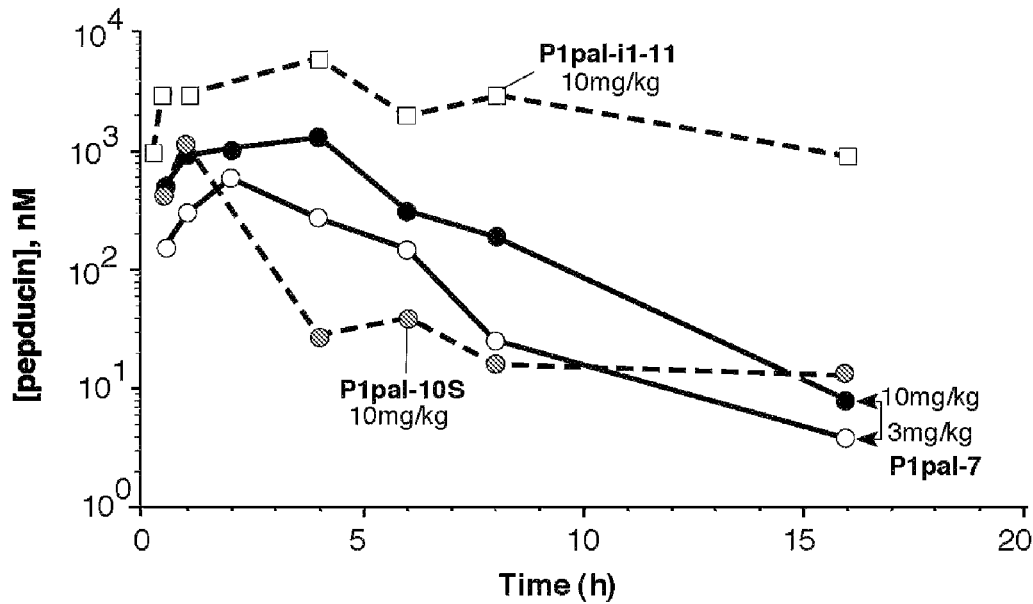
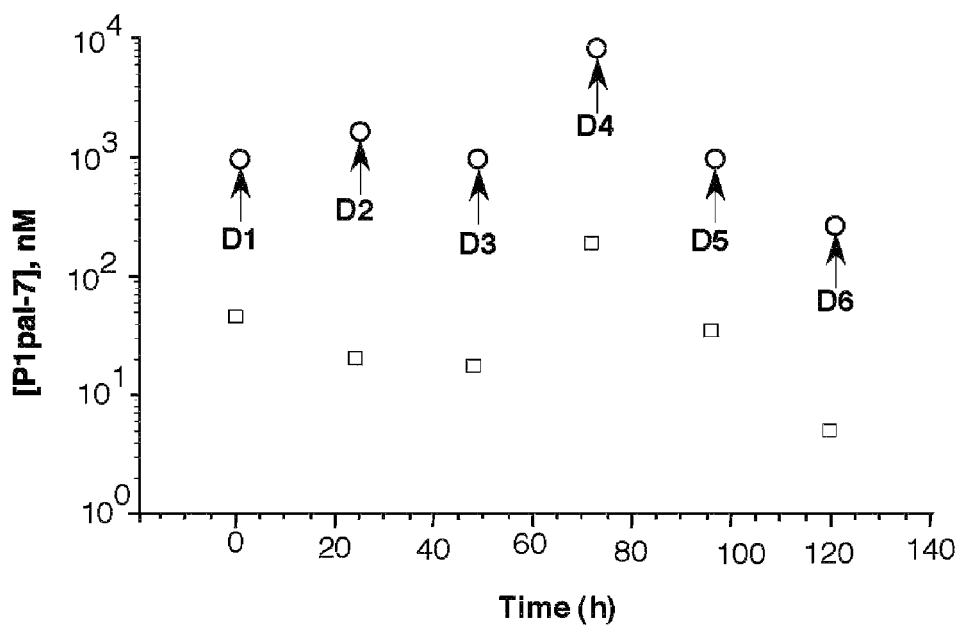

SEQUENCE LISTING

```
<160> NUMBER OF SEQ ID NOS: 46

<210> SEQ ID NO 1
<211> LENGTH: 6
<212> TYPE: PRT
<213> ORGANISM: Human

<400> SEQUENCE: 1

Ser Phe Leu Leu Arg Asn
1               5

<210> SEQ ID NO 2
<211> LENGTH: 6
<212> TYPE: PRT
<213> ORGANISM: Human

<400> SEQUENCE: 2

Thr Phe Leu Leu Arg Asn
1               5

<210> SEQ ID NO 3
<211> LENGTH: 8
<212> TYPE: PRT
<213> ORGANISM: Human

<400> SEQUENCE: 3

Pro Arg Ser Phe Leu Leu Arg Asn
1               5

<210> SEQ ID NO 4
<211> LENGTH: 6
<212> TYPE: PRT
<213> ORGANISM: Human

<400> SEQUENCE: 4

Ser Leu Ile Gly Arg Leu
1               5

<210> SEQ ID NO 5
<211> LENGTH: 6
<212> TYPE: PRT
<213> ORGANISM: Human

<400> SEQUENCE: 5

Ala Tyr Pro Gly Lys Phe
1               5
```

```
<210> SEQ ID NO 6
<211> LENGTH: 22
<212> TYPE: PRT
<213> ORGANISM: Human

<400> SEQUENCE: 6

Asn Arg Ser Ser Lys Gly Arg Ser Leu Ile Gly Lys Val Asp Gly Thr
1               5                   10                  15

Ser His Val Thr Gly Lys
            20

<210> SEQ ID NO 7
<211> LENGTH: 22
<212> TYPE: PRT
<213> ORGANISM: Artificial Sequence
<220> FEATURE:
<223> OTHER INFORMATION: PAR2 fragment with point mutation

<400> SEQUENCE: 7

Asn Arg Ser Ser Lys Gly Ala Ser Leu Ile Gly Lys Val Asp Gly Thr
1               5                   10                  15

Ser His Val Thr Gly Lys
            20

<210> SEQ ID NO 8
<211> LENGTH: 21
<212> TYPE: PRT
<213> ORGANISM: Human

<400> SEQUENCE: 8

Ser Val Gln Arg Tyr Trp Val Ile Val Asn Pro Met Gly His Ser Arg
1               5                   10                  15

Lys Lys Ala Asn Ile
            20

<210> SEQ ID NO 9
<211> LENGTH: 21
<212> TYPE: PRT
<213> ORGANISM: Artificial Sequence
<220> FEATURE:
<223> OTHER INFORMATION: PAR2 fragment with point mutations

<400> SEQUENCE: 9

Ser Val Arg Gln Tyr Trp Val Ile Val Asn Pro Met Gly His Ser Arg
1               5                   10                  15

Lys Lys Ala Asn Ile
            20

<210> SEQ ID NO 10
<211> LENGTH: 22
<212> TYPE: PRT
<213> ORGANISM: Human

<400> SEQUENCE: 10

Ile Arg Met Leu Arg Ser Ser Ala Met Asp Glu Asn Ser Glu Lys Lys
1               5                   10                  15

Arg Lys Arg Ala Ile Lys
            20

<210> SEQ ID NO 11
<211> LENGTH: 22
<212> TYPE: PRT
<213> ORGANISM: Artificial Sequence
```

```
<220> FEATURE:
<223> OTHER INFORMATION: PAR2 fragment with point mutation

<400> SEQUENCE: 11

Ile Arg Met Leu Arg

<223> OTHER INFORMATION: PAR2 fragment with mutations

<400> SEQUENCE: 16

Phe Val Ser Ala Ala Ala Leu Cys Arg Ser Val Arg Thr
1               5                   10

<210> SEQ ID NO 17
<211> LENGTH: 21
<212> TYPE: PRT
<213> ORGANISM: Human

<400> SEQUENCE: 17

Arg Met Leu Arg Ser Ser Ala Met Asp Glu Asn Ser Glu Lys Lys Arg
1               5                   10                  15

Lys Arg Ala Ile Lys
            20

<210> SEQ ID NO 18
<211> LENGTH: 21
<212> TYPE: PRT
<213> ORGANISM: Artificial Sequence
<220> FEATURE:
<223> OTHER INFORMATION: PAR2 fragment with mutation

<400> SEQUENCE: 18

Arg Met Leu Arg Ser Ser Ala Met Asp Glu Asn Ser Glu Lys Lys Arg
1               5                   10                  15

Lys Arg Ala Ile Phe
            20

<210> SEQ ID NO 19
<211> LENGTH: 18
<212> TYPE: PRT
<213> ORGANISM: Artificial Sequence
<220> FEATURE:
<223> OTHER INFORMATION: PAR2 fragment with mutation

<400> SEQUENCE: 19

Arg Ser Ser Ala Met Asp Glu Asn Ser Glu Lys Lys Arg Lys Arg Ala
1               5                   10                  15

Ile Phe

<210> SEQ ID NO 20
<211> LENGTH: 18
<212> TYPE: PRT
<213> ORGANISM: Artificial Sequence
<220> FEATURE:
<223> OTHER INFORMATION: PAR2 fragment with mutation

<400> SEQUENCE: 20

Arg Ser Ser Ala Met Asp Glu Asn Ser Glu Lys Lys Arg Lys Ser Ala
1               5                   10                  15

Ile Lys

<210> SEQ ID NO 21
<211> LENGTH: 18
<212> TYPE: PRT
<213> ORGANISM: Artificial Sequence
<220> FEATURE:
<223> OTHER INFORMATION: PAR2 fragment with mutation

<400> SEQUENCE: 21

Arg Ser Ser Ala Met Asp Glu Asn Ser Glu Lys Lys Arg Lys Ser Ala
1               5                   10                  15

Ile Phe

<210> SEQ ID NO 22
<211> LENGTH: 18
<212> TYPE: PRT
<213> ORGANISM: Artificial Sequence
<220> FEATURE:
<223> OTHER INFORMATION: PAR2 fragment with mutation

<400> SEQUENCE: 22

Arg Ser Ser Ala Met Asp Glu Asn Ser Glu Lys Lys Arg Lys Gln Ala
1               5                   10                  15

Ile Lys

<210> SEQ ID NO 23
<211> LENGTH: 14
<212> TYPE: PRT
<213> ORGANISM: Artificial Sequence
<220> FEATURE:
<223> OTHER INFORMATION: PAR2 fragment with mutation

<400> SEQUENCE: 23

Gly Asp Glu Asn Ser Glu Lys Lys Arg Lys Arg Ala Ile Phe
1               5                   10

<210> SEQ ID NO 24
<211> LENGTH: 14
<212> TYPE: PRT
<213> ORGANISM: Artificial Sequence
<220> FEATURE:
<223> OTHER INFORMATION: PAR2 fragment with mutation

<400> SEQUENCE: 24

Gly Asp Glu Asn Ser Glu Lys Lys Arg Lys Gln Ala Ile Lys
1               5                   10

<210> SEQ ID NO 25
<211> LENGTH: 7
<212> TYPE: PRT
<213> ORGANISM: Human

<400> SEQUENCE: 25

Lys Lys Ser Arg Ala Leu Phe
1               5

<210> SEQ ID NO 26
<211> LENGTH: 10
<212> TYPE: PRT
<213> ORGANISM: Artificial Sequence
<220> FEATURE:
<223> OTHER INFORMATION: PAR1 fragment with mutation

<400> SEQUENCE: 26

Asn Arg Ser Lys Lys Ser Ser Ala Leu Phe
1               5                   10

<210> SEQ ID NO 27
<211> LENGTH: 19
<212> TYPE: PRT
<213> ORGANISM: Artificial Sequence
<220> FEATURE:
<223> OTHER INFORMATION: PAR1 fragment with mutations

<400> SEQUENCE: 27

Glu Cys Glu Ser Ser Ser Ala Glu Ala Asn Arg Ser Lys Lys Glu Arg

-continued

```
                1               5                  10                  15

Glu Leu Phe

<210> SEQ ID NO 28
<211> LENGTH: 11
<212> TYPE: PRT
<213> ORGANISM: Human

<400> SEQUENCE: 28

Ile Leu Lys Met Lys Val Lys Lys Pro Ala Val
 1               5                  10

<210> SEQ ID NO 29
<211> LENGTH: 6
<212> TYPE: PRT
<213> ORGANISM: Human

<400> SEQUENCE: 29

Ser Leu Ile Gly Lys Val
 1               5

<210> SEQ ID NO 30
<211> LENGTH: 8
<212> TYPE: PRT
<213> ORGANISM: Human

<400> SEQUENCE: 30

Pro Arg Ser Phe Leu Leu Arg Asn
 1               5

<210> SEQ ID NO 31
<211> LENGTH: 79
<212> TYPE: PRT
<213> ORGANISM: Bovine

<400> SEQUENCE: 31

Glu Ser Phe Val Ile Tyr Met Phe Val Val His Phe Ile Ile Pro Leu
 1               5                  10                  15

Ile Val Ile Phe Phe Cys Tyr Gly Gln Leu Val Phe Thr Val Lys Glu
                20                  25                  30

Ala Ala Ala Gln Gln Gln Glu Ser Ala Thr Thr Gln Lys Ala Glu Lys
            35                  40                  45

Glu Val Thr Arg Met Val Ile Ile Met Val Ile Ala Phe Leu Ile Cys
        50                  55                  60

Trp Leu Pro Tyr Ala Gly Val Ala Phe Tyr Ile Phe Thr His Gln
    65                  70                  75

<210> SEQ ID NO 32
<211> LENGTH: 73
<212> TYPE: PRT
<213> ORGANISM: Human

<400> SEQUENCE: 32

Ala Tyr Tyr Phe Ser Ala Phe Ser Ala Val Phe Phe Phe Val Pro Leu
 1               5                  10                  15

Ile Ile Ser Thr Val Cys Tyr Val Ser Ile Ile Arg Cys Leu Ser Ser
                20                  25                  30

Ser Ala Val Ala Asn Arg Ser Lys Lys Ser Arg Ala Leu Phe Leu Ser
            35                  40                  45

Ala Ala Val Phe Cys Ile Phe Ile Ile Cys Phe Gly Pro Thr Asn Val
        50                  55                  60
```

-continued

Leu Leu Ile Ala His Tyr Ser Phe Leu
65                  70

<210> SEQ ID NO 33
<211> LENGTH: 73
<212> TYPE: PRT
<213> ORGANISM: Baboon

<400> SEQUENCE: 33

Ala Tyr Tyr Phe Ser Ala Phe Ser Ala Val Phe Phe Val Pro Leu
1               5                   10                  15

Ile Ile Ser Thr Val Cys Tyr Val Ser Ile Ile Arg Cys Leu Ser Ser
                20                  25                  30

Ser Thr Val Ala Asn Arg Ser Lys Lys Ser Arg Ala Leu Phe Leu Ser
            35                  40                  45

Ala Ala Val Phe Cys Ile Phe Ile Ile Cys Phe Gly Pro Thr Asn Ile
        50                  55                  60

Leu Leu Ile Ala His Tyr Ser Phe Leu
65                  70

<210> SEQ ID NO 34
<211> LENGTH: 73
<212> TYPE: PRT
<213> ORGANISM: Rat

<400> SEQUENCE: 34

Ser Tyr Tyr Phe Ser Ala Phe Ser Ala Ile Phe Phe Leu Val Pro Leu
1               5                   10                  15

Ile Ile Ser Thr Val Cys Tyr Thr Ser Ile Ile Arg Cys Leu Ser Ser
                20                  25                  30

Ser Ala Val Ala Asn Arg Ser Lys Lys Ser Arg Ala Leu Phe Leu Ser
            35                  40                  45

Ala Ala Val Phe Cys Ile Phe Ile Val Cys Phe Gly Pro Thr Asn Val
        50                  55                  60

Leu Leu Ile Val His Tyr Leu Leu Leu
65                  70

<210> SEQ ID NO 35
<211> LENGTH: 73
<212> TYPE: PRT
<213> ORGANISM: Mouse

<400> SEQUENCE: 35

Ser Tyr Tyr Phe Ser Ala Phe Ser Ala Ile Phe Phe Leu Val Pro Leu
1               5                   10                  15

Ile Val Ser Thr Val Cys Tyr Ser Ser Ile Ile Arg Cys Leu Ser Ser
                20                  25                  30

Ser Ala Val Ala Asn Arg Ser Lys Lys Ser Arg Ala Leu Phe Leu Ser
            35                  40                  45

Ala Ala Val Phe Cys Ile Phe Ile Val Cys Phe Gly Pro Thr Asn Val
        50                  55                  60

Leu Leu Ile Val His Tyr Leu Phe Leu
65                  70

<210> SEQ ID NO 36
<211> LENGTH: 73
<212> TYPE: PRT
<213> ORGANISM: Hamster

```
<400> SEQUENCE: 36

Ser Tyr Tyr Phe Ser Ala Phe Ser Ala Val Phe Phe Leu Val Pro Leu
1               5                   10                  15

Ile Ile Ser Thr Ile Cys Tyr Met Ser Ile Ile Arg Cys Leu Ser Ser
            20                  25                  30

Ser Ser Val Ala Asn Arg Ser Lys Lys Ser Arg Ala Leu Phe Leu Ser
        35                  40                  45

Ala Ala Val Phe Cys Val Phe Ile Val Cys Phe Gly Pro Thr Asn Val
    50                  55                  60

Leu Leu Ile Met His Tyr Leu Leu Leu
65                  70

<210> SEQ ID NO 37
<211> LENGTH: 70
<212> TYPE: PRT
<213> ORGANISM: Xenopus

<400> SEQUENCE: 37

Ile Tyr Tyr Phe Ser Ser Phe Cys Leu Leu Phe Phe Val Pro Phe
1               5                   10                  15

Ile Ile Thr Thr Ile Cys Tyr Ile Gly Ile Ile Arg Ser Leu Ser Ser
            20                  25                  30

Ser Ser Ile Glu Asn Ser Cys Lys Lys Thr Arg Ala Leu Phe Leu Ala
        35                  40                  45

Val Val Val Leu Cys Val Phe Ile Ile Cys Phe Gly Pro Thr Asn Val
    50                  55                  60

Leu Phe Leu Thr His Tyr
65                  70

<210> SEQ ID NO 38
<211> LENGTH: 75
<212> TYPE: PRT
<213> ORGANISM: Human

<400> SEQUENCE: 38

Phe Asn Tyr Phe Leu Ser Leu Ala Ile Gly Val Phe Leu Phe Pro Ala
1               5                   10                  15

Phe Leu Thr Ala Ser Ala Tyr Val Leu Met Ile Arg Met Leu Arg Ser
            20                  25                  30

Ser Ala Met Asp Glu Asn Ser Glu Lys Lys Arg Lys Arg Ala Ile Lys
        35                  40                  45

Leu Ile Val Thr Val Leu Ala Met Tyr Leu Ile Cys Phe Thr Pro Ser
    50                  55                  60

Asn Leu Leu Leu Val Val His Tyr Phe Leu Ile
65                  70                  75

<210> SEQ ID NO 39
<211> LENGTH: 75
<212> TYPE: PRT
<213> ORGANISM: Mouse

<400> SEQUENCE: 39

Phe Asn Tyr Phe Leu Ser Leu Ala Ile Gly Val Phe Leu Phe Pro Ala
1               5                   10                  15

Leu Leu Thr Ala Ser Ala Tyr Val Leu Met Ile Lys Thr Leu Arg Ser
            20                  25                  30

Ser Ala Met Asp Glu His Ser Glu Lys Lys Arg Gln Arg Ala Ile Arg
        35                  40                  45
```

```
Leu Ile Ile Thr Val Leu Ala Met Tyr Phe Ile Cys Phe Ala Pro Ser
        50                  55                  60

Asn Leu Leu Val Val His Tyr Phe Leu Ile
 65              70                  75

<210> SEQ ID NO 40
<211> LENGTH: 75
<212> TYPE: PRT
<213> ORGANISM: Rat

<400> SEQUENCE: 40

Phe Ser Tyr Phe Leu Ser Leu Ala Ile Gly Val Phe Leu Phe Pro Ala
 1               5                  10                  15

Leu Leu Thr Ala Ser Ala Tyr Val Leu Met Ile Lys Thr Leu Arg Ser
        20                  25                  30

Ser Ala Met Asp Glu His Ser Glu Lys Lys Arg Arg Arg Ala Ile Arg
        35                  40                  45

Leu Ile Ile Thr Val Leu Ser Met Tyr Phe Ile Cys Phe Ala Pro Ser
        50                  55                  60

Asn Val Leu Val Val His Tyr Phe Leu Ile
 65              70                  75

<210> SEQ ID NO 41
<211> LENGTH: 69
<212> TYPE: PRT
<213> ORGANISM: Human

<400> SEQUENCE: 41

Leu Tyr Tyr Phe Ile Ser Leu Ala Phe Phe Gly Phe Leu Ile Pro Phe
 1               5                  10                  15

Val Leu Ile Ile Tyr Cys Tyr Ala Ala Ile Ile Arg Thr Leu Asn Ala
        20                  25                  30

Tyr Asp His Arg Trp Leu Trp Tyr Val Lys Ala Ser Leu Leu Ile Leu
        35                  40                  45

Val Ile Phe Thr Ile Cys Phe Ala Pro Ser Asn Ile Ile Leu Ile Ile
        50                  55                  60

His His Ala Asn Tyr
 65

<210> SEQ ID NO 42
<211> LENGTH: 69
<212> TYPE: PRT
<213> ORGANISM: Rat

<400> SEQUENCE: 42

Phe Tyr Tyr Phe Val Ser Leu Ala Phe Phe Gly Phe Leu Ile Pro Phe
 1               5                  10                  15

Val Val Ser Val Phe Cys Tyr Thr Thr Leu Ile His Lys Leu Asn Ala
        20                  25                  30

Gln Asp Arg Lys Trp Leu Arg Tyr Ile Lys Ala Val Leu Leu Ile Leu
        35                  40                  45

Val Ile Phe Thr Ile Cys Phe Ala Pro Thr Asn Ile Ile Leu Ile Ile
        50                  55                  60

His His Ala Asn Tyr
 65

<210> SEQ ID NO 43
<211> LENGTH: 69
```

```
<212> TYPE: PRT
<213> ORGANISM: Mouse

<400> SEQUENCE: 43

Phe Tyr Tyr Phe Val Ser Leu Ala Phe Phe Gly Phe Leu Ile Pro Phe
1               5                   10                  15

Val Ile Ile Ile Phe Cys Tyr Thr Thr Leu Ile His Lys Leu Lys Ser
            20                  25                  30

Lys Asp Arg Ile Trp Leu Gly Tyr Ile Lys Ala Val Leu Leu Ile Leu
        35                  40                  45

Val Ile Phe Thr Ile Cys Phe Ala Pro Thr Asn Ile Ile Leu Val Ile
    50                  55                  60

His His Ala Asn Tyr
65

<210> SEQ ID NO 44
<211> LENGTH: 69
<212> TYPE: PRT
<213> ORGANISM: Human

<400> SEQUENCE: 44

Gln Pro Ala Phe Thr Cys Leu Ala Leu Leu Gly Cys Phe Leu Pro Leu
1               5                   10                  15

Leu Ala Met Leu Leu Cys Tyr Gly Ala Thr Leu His Thr Leu Ala Ala
            20                  25                  30

Ser Gly Arg Arg Tyr Gly His Ala Leu Arg Leu Thr Ala Val Val Leu
        35                  40                  45

Ala Ser Ala Val Ala Phe Phe Val Pro Ser Asn Leu Leu Leu Leu Leu
    50                  55                  60

His Tyr Ser Asp Pro
65

<210> SEQ ID NO 45
<211> LENGTH: 69
<212> TYPE: PRT
<213> ORGANISM: Mouse

<400> SEQUENCE: 45

Arg Pro Ala Phe Ile Cys Leu Ala Val Leu Gly Cys Phe Val Pro Leu
1               5                   10                  15

Leu Ala Met Gly Leu Cys Tyr Gly Ala Thr Leu Arg Ala Leu Ala Ala
            20                  25                  30

Asn Gly Gln Arg Tyr Ser His Ala Leu Arg Leu Thr Ala Leu Val Leu
        35                  40                  45

Phe Ser Ala Val Ala Ser Phe Thr Pro Ser Asn Val Leu Leu Val Leu
    50                  55                  60

His Tyr Ser Asn Pro
65

<210> SEQ ID NO 46
<211> LENGTH: 69
<212> TYPE: PRT
<213> ORGANISM: Rat

<400> SEQUENCE: 46

Arg Pro Ala Phe Ile Cys Leu Ala Val Leu Gly Cys Phe Val Pro Leu
1               5                   10                  15

Leu Ala Met Val Leu Cys Tyr Gly Ala Thr Leu Arg Ala Leu Ala Ala
            20                  25                  30
```

```
Asn Gly Gln Arg Tyr Ser His Ala Val Arg Leu Thr Ala Leu Val Leu
        35                  40                  45
Phe Ser Ala Val Ala Ala Phe Thr Pro Ser Asn Val Leu Leu Val Leu
    50                  55                  60
His Tyr Ser Asn Pro
65
```

PEPDUCIN DESIGN AND USE

CROSS-REFERENCE TO RELATED APPLICATIONS

This application is a national phase application under 35 U.S.C. 371 of international application PCT/US2012/032824, filed Apr. 9, 2012 which claims priority to and the benefit of U.S. Provisional Application Ser. No. 61/473,675 of the same title and filed on Apr. 8, 2011, the entire content of which is incorporated herein by reference.

STATEMENT REGARDING FEDERALLY FUNDED RESEARCH AND DEVELOPMENT

This invention was made with Government support under Grants R01 HL057905, HL064701, CA122992, and CA104406 awarded by the National Institutes of Health. The government has certain rights in this invention.

FIELD OF INVENTION

The invention relates generally to G protein coupled receptors and in particular to antagonists of G protein receptors and methods of making and using the same.

BACKGROUND

A variety of hormones, neurotransmitters and biologically active substances control, regulate, or adjust the functions of living bodies via specific receptors located in cell membranes. In eukaryotes including yeasts and mammals, many of these receptors mediate the transmission of intracellular signals by activating guanine nucleotide-binding proteins (G proteins) to which the receptor is coupled. Such receptors are generically referred to as G protein coupled receptors (GPCRs), also known as G protein-linked receptors (GPLR) or seven-transmembrane domain receptors. Binding of a specific signaling molecule, i.e., a ligand, to the GPCR can cause a conformational change in the receptor, resulting in a form that is able to bind and activate a G protein, thereby triggering a cascade of intracellular events that eventually leads to a biological response. Typically, GPCRs interact with G proteins to regulate the synthesis of intracellular second messengers such as cyclic AMP, inositol phosphates, diacylglycerol and calcium ions.

Known and uncharacterized GPCRs have been major targets for drug action and development as they are implicated in many diseases (Jacoby et al., *Chem Med Chem* 2006, 1:760-782). GPCRs usually share a common structural motif of seven transmembrane helical domains (TM1 to TM7) connected by three intracellular (IL-1/i1 to IL-3/i3) loops and three extracellular (EL-1/e1 to EL-3/e3) loops. The seven transmembrane helices form a barrel-like cavity within the plasma membrane and it is the conformational change in this structure triggered by extracellular interaction with a ligand that further activates domains for G-protein coupling inside the cell. GPCRs play a vital role in the signaling processes that control cellular metabolism, cell growth and motility, adhesion, inflammation, neuronal signaling, and blood coagulation.

GPCRs, along with G-proteins and effectors (intracellular enzymes and channels modulated by G-proteins), are the components of a modular signaling system that connects the state of intra-cellular second messengers to extra-cellular inputs (Pierce et al., *Nature Rev Mole Cell Bio* 2002, 3, 639-650). The superfamily of GPCR is large, and sequencing of the human genome has revealed over 850 genes that encode them (Hopkins and Groom *Nature Reviews Drug Discovery* 2002, 1, 727-730). GPCRs can be divided into 6 classes based on sequence homology and functional similarity (Foord et al., *Pharmacol Rev* 2005, 57(2): 279-88): Class A (or 1) (Rhodopsin-like), Class B (or 2) (Secretin receptor family), Class C (or 3) (Metabotropic glutamate/pheromone), Class D (or 4) (Fungal mating pheromone receptors), Class E (or 5) (Cyclic AMP receptors) and Class F (or 6) (Frizzled/Smoothened).

Among Rhodopsin-like GPCRs are protease-activated receptors (PARs). Members of the PAR family act as sensors of extracellular protease gradients, enabling cells to react to the proteolytic microenvironment during a wide range of physiological activities such as tissue remodeling. To date, four different PARs have been identified: PAR1, PAR2, PAR3 and PAR4. Proteases such as trypsin, thrombin, and MMP-1 cleave the N-terminal extracellular domain of individual PAR members, thereby unmasking a tethered ligand that binds to the outer surface of the receptor to activate transmembrane signaling to intracellular G proteins. PAR1 was originally discovered on platelets and serves as the prototype for this specialized class of GPCRs. PAR1 is activated when it is cleaved by thrombin between residues R41-S42 located within the N-terminal extracellular domain of the receptor. PAR3 and PAR4 are also activated by thrombin, whereas PAR2 is a trypsin/tryptase receptor. Proteolytic cleavage exposes a new N-terminus that binds to the body of the receptor in an unusual intra-molecular mode. Synthetic peptides that correspond to the first few amino acids of the freshly cleaved N-terminus of the PARs, e.g. SFLLRN$^{PAR1}$ (SEQ ID NO:1), TFLLRN$^{PAR1}$ (SEQ ID NO:2), PRSFLLRN$^{PAR1}$ (SEQ ID NO:3), SLIGRL$^{PAR2}$ (SEQ ID NO:4), AYPGKF$^{PAR4}$ (SEQ ID NO:5), can also function as selective inter-molecular agonists to PARs.

PAR1, the major thrombin receptor, has been shown to influence a wide range of physiological and pathological processes of the cardiovascular system, including endothelial barrier function, vasoreactivity, intimal hyperplasia, inflammation and hemostasis (Ossovskaya et al., *Physiol Rev* 2004, 84:579-621). PAR1 is a mediator of proliferation and migration of endothelial cells in vitro and is essential for angiogenesis in the developing mouse. PAR1-deficient mice result in lethality of half the embryos at midgestation (E9.5) due to defective blood vessel formation. Surprisingly, PAR1-deficient mice had no altered platelet function phenotypes leading to the discovery of PAR4. Unlike in humans, PAR4 is the major thrombin receptor on mouse platelets and PAR4-deficient mice do not signal to thrombin. PAR2, a cell surface receptor for trypsin-like proteases, is widely expressed in inflammatory cells, stroma, endothelium and intestinal epithelium. PAR2 plays a key role in a number of acute and chronic inflammatory diseases of the joints, lungs, brain, gastrointestinal tract, and vascular systems, and has been implicated in the progression of liver fibrosis. The functional role of PAR3 is unclear and the synthetic PAR3 tethered ligand TFRGAP does not stimulate detectable downstream signaling. PARs have also been shown to form functional heterodimers. PAR1 and PAR3 can serve as co-factors for PAR4, and PAR1 can transactivate PAR2 (Kaneider et al., *Nat Immunol* 2007, 8:1303-12).

Each PAR couples to a distinct subset of G proteins. For instance, PAR1 couples with Ga-subunits $G_q$, $G_i$ and $G_{12/13}$ that are differentially activated by different proteases. Thrombin canconcomitantly activate all three heterotrimeric subunits whereas MMP-1 more selectively activates $G_{12/13}$ signaling. PAR1-$G_q$ stimulates phospholipase C-β generatation of $InsP_3$ which mobilizes $Ca^{2+}$ and diacylglycerol (DAG) which activates protein kinase C-α (PKCα). These in turn activate phospholipase $A_2$ and phospholipase D. $G_{12/13}$ plays a major role in cell shape change, migration and rho-dependent oncogenesis. Previously it has been shown that a switch in G-protein signaling from $G_{12/13}$ to $G_i$ occurs in the context of PAR1-PAR2 heterodimers is involved in the maintenance of endothelial barrier function. $G_i$ is involved in activation of rac and inhibition of adenylate cyclase and suppression of cAMP. It is still not understood how PAR1 regulates the MAP kinase cascade members such as ERK1/2.

In addition to their well-recognized roles in vascular biology, PARs have also been proposed to be involved in the regulation of survival, apoptosis and tumor growth (e.g., Yang et al., *Cancer Res* 2009, 69:6223-31). PAR1 and PAR2 are important in tumor cell motility in melanoma (Tellez C, et al., *Oncogene* 2003, 22:3130-37) and PAR1 is involved in the invasive and metastatic processes of breast (Henrikson et al., *Br. J. Cancer* 1999, 79:401-06), ovarian (Agarwal et al., *Mol Cancer Ther* 2008, 7:2746-57) and pancreatic cancer (Rudroff et al., *Clin. Exp. Metastasis* 2002, 19:181-89). PAR1 has also been identified as an oncogene in the transformation of NIH3T3 mouse fibroblasts and atopic expression of PAR1 confers tumorigenicity in PAR1-null breast carcinoma cells (Boire et al. *Cell* 2005, 120:303-13). Recent work measured PAR1, PAR4 and VEGF expression in 60 non-small-cell lung cancers (NSCLCs) which consisted of 30 adenocarcinomas and 30 squamous cell carcinomas (Ghio et al., *Clin Lung Cancer* 2006, 7:395-00). It was found that the majority of lung tumors expressed VEGF and that there was a significant correlation between PAR1 and/or PAR-4 expression with VEGF. Moreover, there was a trend towards shorter 3-year survival in PAR1-positive lung cancers.

PAR2 mediates a number of (patho)physiological pathways involved in acute and chronic inflammation, arthritis, allergic reactions, sepsis, inflammatory pain, as well as cancer cell invasion and metastasis (e.g., Kaneider et al., *Nat Med* 2005, 11: 661-665). The pleiotropic downstream pathways activated by PAR2 include calcium mobilization, phospholipase C-b-dependent production of inositol phosphates and diacylglycerol, Rho and Rac activation, MAPK signaling and gene transcription (Ossovskaya et al., 2004, supra).

As a cell surface sensor of proteases, PAR2 endows the cell with the ability to respond or over-respond to the rapidly changing proteolytic microenvironment that occurs during inflammation. PAR2-deficient mice exhibit reduced granulocytic infiltration and tissue damage, and suppression of inflammatory cytokines in models of intestinal inflammation, autoimmunity, and encephalomyelitis (Noorbakhsh, et al., *J Exp Med* 2006, 203:425-35; Cenac et al., *Am J Pathol* 2002, 161:1903-15). Reduced cardiac ischemia/reperfusion injury was also observed in PAR2-deficient mice, which correlated with a decline in inflammatory mediators (Antoniak et al., *Arterioscler Thromb Vasc Biol.* 2010, 30: 2136-42). Conversely, overstimulation of PAR2 can lead to severe edema, granulocyte infiltration, increased tissue permeability, tissue damage and hypotension (Vergnolle et al., *Br J Pharmacol* 1999, 127: 1083-90; Cenac et al., 2002, supra). Agonists of PAR2 including trypsin and the synthetic SLIGRL peptide also trigger the release of calcitonin and substance P from sensory neurons causing neutrophil infiltration, edema, hyperalgesia, and cancer pain (Vergnolle et al., *Nat Med* 2001, 7:821-26; Lam et al., *Pain* 2010, 149: 263-72). PAR2 has been linked to arthritis as evidenced by significant decreases in joint inflammation in PAR2-deficient mice (Ferrell et al. *J Clin Invest* 2003, 111: 35-41) and upregulated expression of the receptor in osteoarthritis and rheumatoid arthritis synovial tissues (Ferrell et al., *Ann Rheum Dis.* 2010, 69: 2051-2054).

Tryptase, a major pro-inflammatory serine protease, can also cleave and activate PAR2. Local or systemic release of high levels of mast cell-derived tryptase can have life-threatening consequences including acute asthma, systemic mastocytosis, and anaphylaxis (Caughey, *Immunol Rev* 2007, 217: 141-54). A specific and effective pharmacological inhibitor of PAR2 therefore has the potential to provide beneficial anti-inflammatory effects and reduce the detrimental activity of mast cells, neutrophils, and other PAR2-expressing leukocytes that contribute to tissue damage. Likewise, with the wide-ranging tumorigenicity discussed above of PAR1 and other PARs, an effective inhibitor of PAR1 and other PARs would be highly therapeutic. To date, however, it has been challenging to identify an effective PAR2 or PAR1 antagonist that lacks agonist activity or is efficacious at sub-millimolar levels (e.g., Goh et al., *Br J Pharmacol* 2009, 158: 1695-1704).

Cell-penetrating peptides or polypeptides called pepducins have been devised by attaching a membrane-penetrating, hydrophobic moiety to peptides derived from a wild-type GPCR, thereby producing manmade agonists and antagonists against specific receptor-G protein signaling pathways (Covic L. et al. 2002, *PNAS* 99: 643-48; U.S. Pat. No. 6,864,229, the disclosure of which are both incorporated herein by reference). These lipidated, chimeric peptides or polypeptides have the ability to rapidly flip across the membrane and interfere with receptor-G protein signaling in a highly specific manner, i.e. with high selectivity for their cognate receptors. Pepducins for PARs, e.g., PAR1, PAR2, and PAR4, cholecystokinins A and B (CCKA, CCKB), somatostatin-2 (SSTR2), melanocortin-4 (MC4R), glucagon-like peptide-1 receptor (GLP-1R), and $P2Y_{12}$ ADP receptor have been made that act as agonists and/or antagonists for the receptors from which they are derived. These compositions are useful for activating or inhibiting the activity of a broad range of GPCRs, including protein family PARs. Human PARs include PAR1 (Genbank Accession Number AF019616), PAR2 (Genbank Accession Number XM003671), PAR3 (Genbank Accession Number NM004101) and PAR4 (Genbank Accession Number NM003950.1), the sequences of which are all incorporated herein by reference.

The application of pepducin technologies in the effort to devise an effective antagonist without significant or substantial agonist effect for members of the PAR family, more broadly, Rhodopsin-like GPCRs, and further more broadly, GPCRs, has so far not yielded satisfactory results. There remains a need for effective GPCR antagonists both for further studying the mechanism of receptor-G protein coupling and its implications on the selective contacts between receptors and G proteins, and to make therapeutics as prophylactics and/or treatments for various diseases or conditions where GPCRs are implicated.

SUMMARY OF THE INVENTION

The present invention discloses a new generation of pepducins based on mutated versions of full-length GPCRs or their fragments. These pepducins, the product of a rational design approach based on stereochemical models of GPCRs, have turned out to be potent and specific. In particular, some of them turned out to be fully antagonistic without any significant agonist activity, and are able to silence otherwise constitutive activities of their cognate GPCRs. Since it has been difficult to provide antagonists against most GPCRs, these new pepducins have provided much needed candidates for effectively targeting the signal transference events regulated by these GPCRs as well as its downstream diseases and conditions.

Accordingly, the present invention, in a first aspect, provides a polypeptide composition with substantial antagonistic effect and no substantial agonistic effect against a G Protein-coupled receptor (GPCR). In some embodiments, these GPCR are otherwise constitutively active, e.g., PAR1 and PAR2. The polypeptide comprises a mutated full-length GPCR or a fragment thereof comprising one or more mutations in a GPCR region selected from the group consisting of (a) the first intracellular loop (i1 loop), (b) the fifth transmembrane helix (TM5), (c) the third intracellular loop (i3 loop), (d) the sixth transmembrane helix (TM6), (e) a fragment of at least three contiguous amino acid residues in sequence found in the i1 loop, TM5, i3 loop and/or TM6, and (f) any combination of (a) to (e). In one feature, the GPCR is a type A, rhodopsin-like GPCR. In some embodiments, the GPCR is a protease-activated receptor (PAR), e.g., PAR1 or PAR2, preferably of human. According to one feature of the invention, at least one of the mutations in the polypeptide is at a position 18 residues N-terminal of the Ballesteros landmark residue 6.50 in the sixth transmembrane helix (TM6). In a further feature, the polypeptide of the present invention further includes a hydrophobic moiety that enables the polypeptide's entry across an intact cell membrane. The mutation may be one of substitution, addition or deletion, where the addition or deletion comprises adding or deleting up to five consecutive residues at the point of mutation in the wild type sequence. In some embodiments, the mutation is a single base substitution.

In one aspect, the present invention provides a chimeric polypeptide that includes two domains: a first domain derived from a GPCR sequence and a second domain, attached to said first domain, that comprises a naturally or non-naturally occurring hydrophobic moiety, which confers cell-penetrating, membrane-tethering properties. The first domain preferably has at least 13 amino acids. In some embodiments of the present invention, the first domain of the chimeric polypeptide does not comprise a native extracellular portion of the wild type sequence, and the chimeric polypeptide binds to its cognate GPCR, e.g., a member of the PAR family. In various embodiments, the hydrophobic moiety is selected from the group consisting of a lipid, an acyl compound and an amino acid.

In one embodiment, the first domain comprises a mutated full-length or fragment of protease-activated receptor-2 (PAR2) and sharing, in sequence, three or more contiguous amino acid residues with a wild type PAR2, e.g., with the i3 loop, TM6, or TM5 of PAR2, wherein at least one mutation in said mutated full-length or fragment of PAR2 is at position 274 or 284. In an embodiment, the PAR2 is a human PAR2. The first domain, in some embodiments, further includes a mutation at position 287. In an embodiment, the mutation is selected from the group consisting of: substituting a methionine (M) at position 274 with another residue, substituting an arginine (R) at position 284 with another residue, and substituting a lysine (K) at position 287 with another residue.

In one embodiment, the first domain of the chimeric polypeptide of the invention comprises a mutated full-length or fragment of protease-activated receptor-2 (PAR2) sharing, in sequence, three or more contiguous amino acid residues with a wild type PAR2, wherein at least two mutations in said mutated full-length or fragment of PAR2 are at position 287 and a second position in the region spanning the fifth transmembrane helix (TM5), the third intracellular loop (i3 loop), and the sixth transmembrane helix (TM6). For example, the second position could be at 274 or 284.

In another embodiment, the first domain of the chimeric polypeptide of the invention comprises a mutated full-length or fragment of protease-activated receptor-1 (PAR1) sharing, in sequence, three or more contiguous amino acid residues with a wild type PAR1, wherein at least one mutation in said mutated full-length or fragment of PAR1 is at position 310. In an embodiment, the PAR2 is a human PAR1.

In another embodiment, the first domain of the chimeric polypeptide of the invention is selected from the group consisting of:

(i) a mutated full-length or fragment of protease-activated receptor (PAR) sharing, in sequence, three or more contiguous amino acid residues with a wild type PAR, wherein at least one mutation in said mutated full-length or fragment of PAR is at a position 18 residues N-terminal of the Ballesteros landmark residue 6.50 in the sixth transmembrane helix (TM6), or at positions corresponding to 248 of bovine rhodopsin when the third intracellular loop (i3 loop) of the PAR is aligned with the i3 loop of bovine rhodopsin;

(ii) a variant of the mutated full-length or fragment of PAR according to (i) wherein up to 40% of the amino acids of the wild type sequence have been replaced with a naturally or non-naturally occurring amino acid or with a peptidomimetic moiety; and/or up to 40% of the amino acids have their side chains chemically modified; and/or up to 20% of the amino acids have been deleted, provided that at least 50% of the amino acids in the third intracellular loop (i3 loop) remain unaltered in the variant;

(iii) a peptide sequence according to (i) or (ii) wherein at least one of the amino acids is replaced with a corresponding D-amino acid;

(iv) a peptide sequence according to any one of (i)-(iii) wherein at least one of the peptidic backbones has been altered to a non-naturally occurring peptidic backbone;

(v) a peptide sequence being the sequence of any one of (i)-(iv) in reverse order; and (vi) a combination of two or more of the peptide sequences of (i) to (v). Said PAR may be selected from the group consisting of PAR1, PAR2, PAR3 and PAR4.

In a second aspect, the present invention provides pharmaceutical composition comprising the chimeric polypeptide of the invention and a pharmaceutically-acceptable excipient, carrier, or diluent. The pharmaceutical composition is preferably suitable for oral, nasal, topical, rectal, vaginal or parenteral administration, or intravenous, subcutaneous or intramuscular injection.

In a third aspect, the present invention provides methods of treating various conditions using compositions of the invention. In an embodiment, a therapeutically effective amount of the chimeric polypeptide where the first domain comprises a mutated full-length or fragment of PAR1 is administered to a mammal in need to treat lung cancer. In another embodiment, a method is provided to treat an ill condition in a mammal that implicates inflammation by administering to said mammal a therapeutically effective amount of a chimeric polypeptide of the invention where the first domain comprises a mutated full-length or fragment of PAR2 sharing, in sequence, three or more contiguous amino acid residues with a wild type PAR2, wherein at least one mutation in said mutated full-length or fragment PAR2 is at a position selected from the group consisting of 274, 284 and 287. The treatable ill condition may be any of the following: pancreatitis, asthma, rheumatoid arthritis, osteoarthritis, cancer, chronic pain, visceral pain, cancer pain, multiple sclerosis, Inflammatory Bowel Disease, Irritable Bowel Syndrome, mast-cell diseases, Mastocytosis, Gout, sepsis, arterial restenosis, atherosclerosis, inflammatory diseases of the airways and gastrointestinal tract, itching, ichthyoses, pruritis, inflammatory skin diseases, psoriasis, and Alzheimer's Disease. Cancers to be treated by this method include cancers of the colon, skin, melanocytes, breast, prostate, central nervous system, brain, immune system, pancreas, head and neck, esophagus, kidney, reproductive system, ovary, endometrium, and cervix.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification, including definitions, will control. In addition, the materials, methods, and examples are illustrative only and not intended to be limiting. All patents and publications cited in this specification are incorporated herein by reference to the extent permitted by applicable law.

Figure 1:
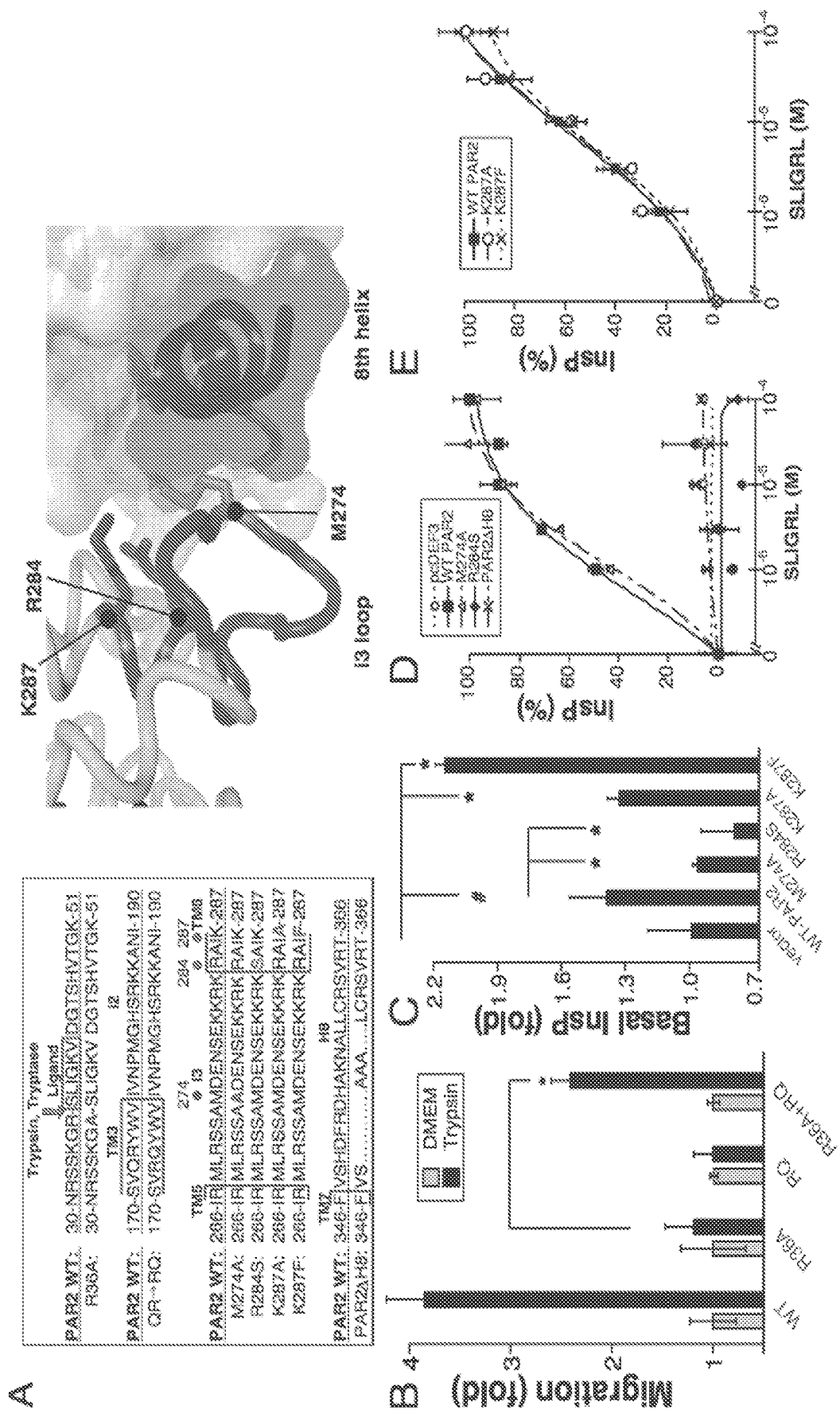
FIG. 1 illustrates that constitutive and ligand-dependent activity of PAR2 is regulated by juxtamembrane residues located in the third intracellular (i3) loop. (A) Location of PAR2 mutants and model of the receptor dimer used in this study. (B) Migration of HEK cells transiently transfected with PAR2 (wild-type, WT), PAR2-R36A, PAR2-RQ, or PAR2-R36A plus PAR2-RQ toward chemotactic gradients of 30 nM trypsin or DMEM media alone for 18 h in a transwell apparatus (8-μM pore), n=2, repeated three independent times. (C-E) Constitutive and SLIGRL-activated signaling of PAR2 mutants to PLC-β. PLC-β activity was measured by [$^3$H]-InsP formation over 30 min and was typically stimulated 4-5 fold above basal with 30-100 μM SLIGRL. Mean PAR2 mutant surface expression was assessed by FACS and was at comparable levels to wild-type in COS cells and in HEK cells. Data (n=2-8) represent the mean±SD. For "*": P<0.05 and "⁴": P=0.07. (F) Co-immunoprecipitation of PAR2-myc with T7-PAR2 in COS7 cells. T7-agarose beads were used to immunoprecipitate associated PAR2-myc as shown by myc immunoblots (top). Immunoblot of T7 confirmed the presence of T7-PAR2 (bottom).

Amino acid sequences shown in the left panel of FIG. 1A are hereby referenced as follows (from top to bottom):
PAR2WT: SEQ ID NO:6;
R36A: SEQ ID NO:7;
PAR2WT: SEQ ID NO:8;
QR-->RQ: SEQ ID NO:9;
PAR2WT: SEQ ID NO:10;
M274A: SEQ ID NO:11;
R284S: SEQ ID NO:12;
K287A: SEQ ID NO:13;
K287F: SEQ ID NO:14;
PAR2WT: SEQ ID NO:15; and
PAR2$_A$H8: SEQ ID NO:16.

Figure 2:
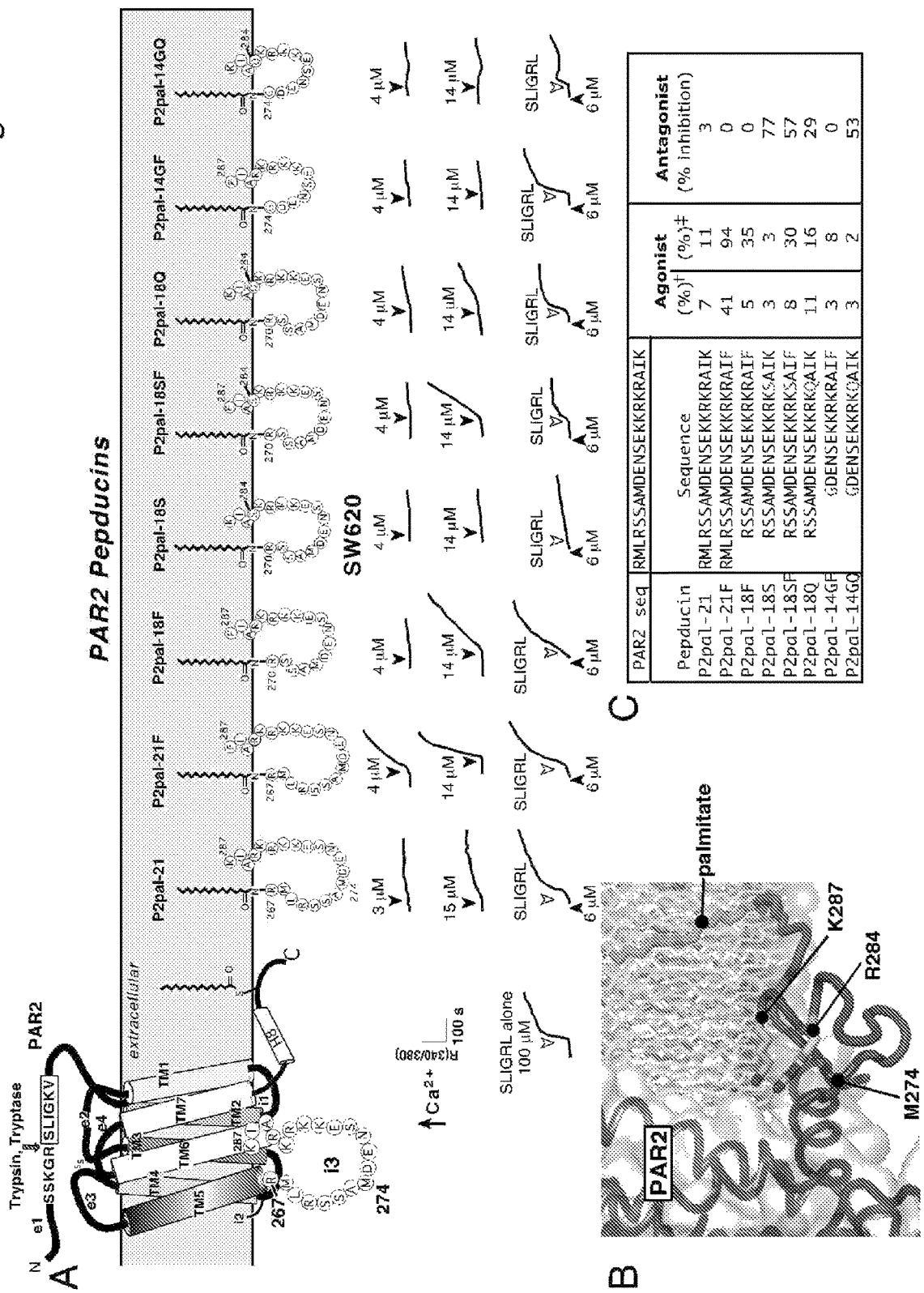

FIG. 2 illustrates the constructs used and the resulting data in the design and screening of agonist and antagonist pepducins. (A) Agonist and antagonist activity of third intracellular (i3) loop PAR2 pepducins (structure shown on top) using calcium flux assays with SW620 colon adenocarcinoma cells that endogenously express PAR2. Each column of three calcium flux traces corresponds to the i3 pepducin sequence shown above. The top row is the agonist activity of 3-4 μM pepducin and the middle row is the agonist activity of 14-15 μM pepducin. The bottom row depicts the calcium signal of 100 μM SLIGRL (open arrow) following 1 min pretreatment with 6 μM pepducin (closed arrow). Final concentration of DMSO vehicle was 0.2%. (B) Model of the WT PAR2 i3 pepducin P2pal-21 bound to the intracellular surface of PAR2. The location of the i3 pepducin was derived by substituting the coordinates of the i3 loop on the intact receptor with the i3 pepducin using the PAR2 dimer model. Key pharmacophore residues M274, R284 and K287, and the palmitate domain are shown. (C) Agonist activity for each pepducin from (A) is reported as initial velocity of calcium flux at 4 μM pepducin (†), or at 14-15 μM pepducin (‡). Antagonist activity of 6 μM pepducin against 100 μM SLIGRL (SEQ ID NO:4), was measured by area under the curve of calcium flux from the bottom row of A. Experiments were repeated at least 2-3 times each and gave highly similar results.

Amino acid sequences shown in FIGS. 2A and 2C are hereby referenced as follows:
PAR2 seq: SEQ ID NO:17;
P2pal-21: SEQ ID NO:17;
P2pal-21F: SEQ ID NO:18;
P2pal-18F: SEQ ID NO:19;
P2pal-18S: SEQ ID NO:20;
P2pal-18SF: SEQ ID NO:21;
P2pal-18Q: SEQ ID NO:22;
P2pal-14GF: SEQ ID NO:23; and
P2pal-14GQ: SEQ ID NO:24.

Figure 3:
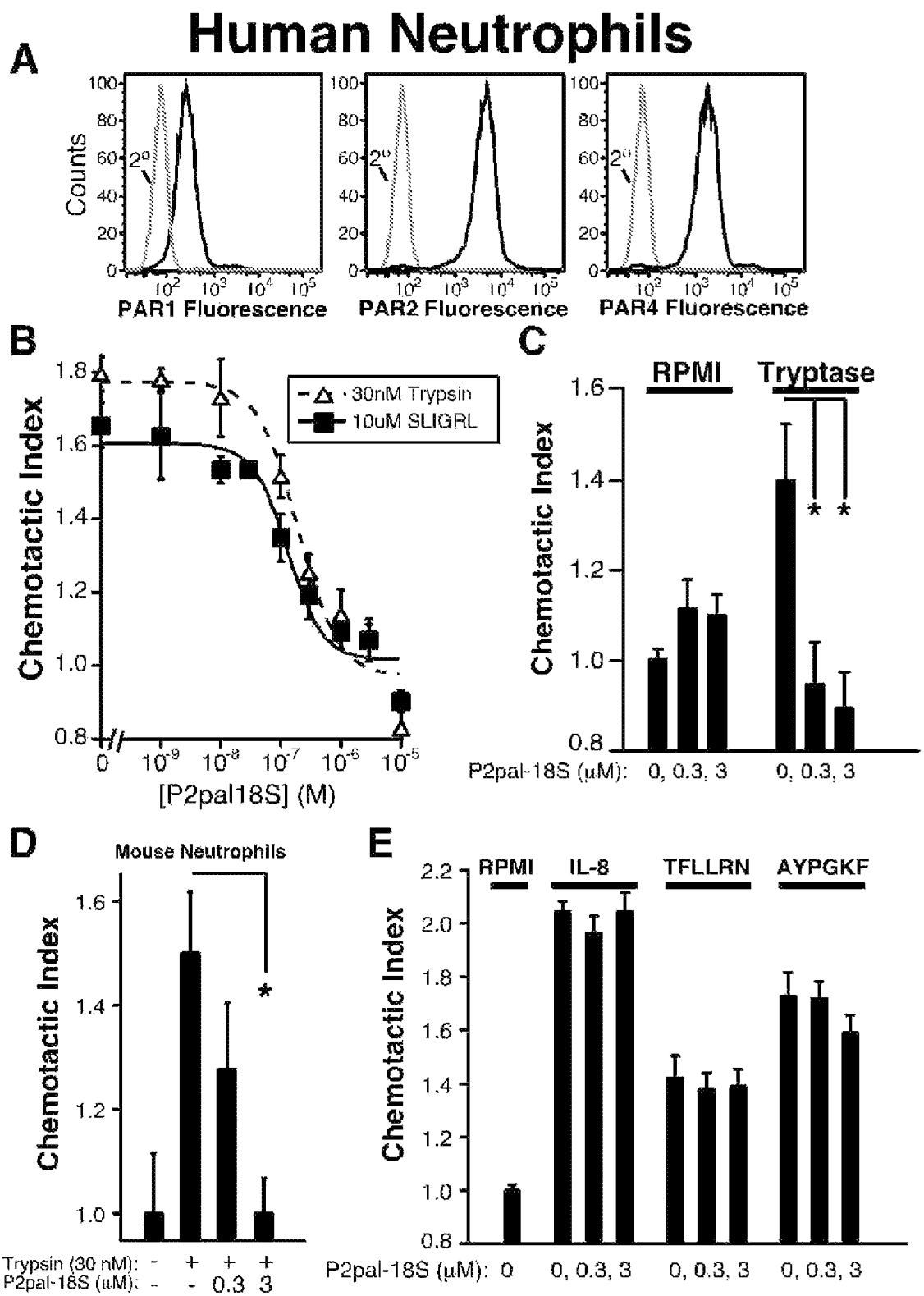

FIG. 3 illustrates data showing that the P2pal-18S pepducin is a full antagonist of PAR2-dependent neutrophil chemotaxis. (A) Human neutrophils (n=4 normal volunteers) were analyzed for surface expression of human PAR1, PAR2, and PAR4 by flow cytometry with PAR-specific antibodies. (B) P2pal-18S inhibits human neutrophil chemotaxis to gradients of trypsin (30 nM) and SLIGRL (SEQ ID NO:4) (10 μM) with IC$_{50}$ values of 0.14-0.2 μM. Chemotaxis index is the ratio of directed versus random migration over 30 min through a 5-μm pore filter. (C) P2pal-18S completely inhibits human neutrophil chemotaxis to 100 nM tryptase. (D) P2pal-18S completely inhibits mouse neutrophil (n=6) chemotaxis to 30 nM trypsin. (E) P2pal-18S does not affect human neutrophil chemotaxis to gradients of 100 nM IL-8 (CXCR1/CXCR2), 10 μM TFLLRN (PAR1) (SEQ ID NO:2), or 100 μM AYPGKF (PAR4) (SEQ ID NO:5). n=4-6, mean±SEM. *, P<0.05.

FIG. 4 shows that specificity of P2pal-18S and P2pal-14GQ pepducins for PAR2 but not the closely related PAR1 and PAR4 receptors. (A) PAR2 antagonist pepducins P2pal-18S and P2pal-14GQ inhibit calcium flux induced by PAR2 (SLIGRL) (SEQ ID NO:4) but not PAR1 (TFLLRN) (SEQ ID NO:2) agonists. SW620 cells were stably transfected with PAR1 and pretreated for 1 min with various concentrations of P2pal-18S or P2pal-14GQ and then stimulated with 30 μM PAR agonist. The IC$_{50}$ of P2pal-18S was 4.0 mM±0.4 mM and P2pa114GQ was 8.0 mM±1.0 mM. (B) P2pal-18S and P2pal-14GQ do not inhibit InsP signaling from PAR1 or PAR4 transiently transfected into COS7 cells. Cells were stimulated with 1 µM TFLLRN (SEQ ID NO:2), 1 µM SLIGRL (SEQ ID NO:4) or 100 µM AYPGKF (SEQ ID NO:5) and [$^3$H]-InsP formation measured over 30 min. (C) SW620 cells were treated with the indicated concentrations of P2pal-18S or P2pal-14GQ in the upper well of an 8-µm pore Boyden chamber and allowed to migrate for 18 h towards 10 µM of the PAR2 specific agonist SLIGRL in the lower chamber. The migration to RPMI/0.1% FBS represents random migration. (D) Migration of HEK cells transiently transfected with PAR2 (wild-type, WT), or PAR2-R36A/PAR2-RQ toward chemotactic gradients of 30 nM trypsin in the absence or presence of the indicated concentration of P2pal-18S for 18 h in a transwell apparatus (8-mM pore). Data (n=2-4) are mean±SEM. *, P<0.05 and **, P<0.005.

FIG. 5 illustrates: (A) PAR1-dependent human platelet aggregation is not affected by P2pal-18S. Gel-filtered platelets were incubated with 2.5 µM SFLLRN (SEQ ID NO:1) to induce PAR1-dependent platelet aggregation. Addition of 1 µM or 5 µM P2pal-18S did not affect the aggregation of the platelets. RWJ 58250, a small molecule PAR1 inhibitor, was used to show that specific blockade of PAR1 would in fact inhibit aggregation of the platelets. Error bars represent mean±SD. (B) P2pal-18S and P2pal-14GQ do not induce apoptosis in SW620 cells. Cells were lifted and incubated in PBS/0.4% BSA for 30 min at 25° C. with 0.5-30 µM P2pal-18S or P2pal-14GQ. Propidium iodide (PI) was added directly to the cells and after a 15 min incubation, PI uptake was quantified by flow cytometry. PI uptake was not significantly different when pepducin was added to the cells as compared to untreated and 0.2% DMSO vehicle treated cells. Error bars represent ±SEM.

Figure 6:
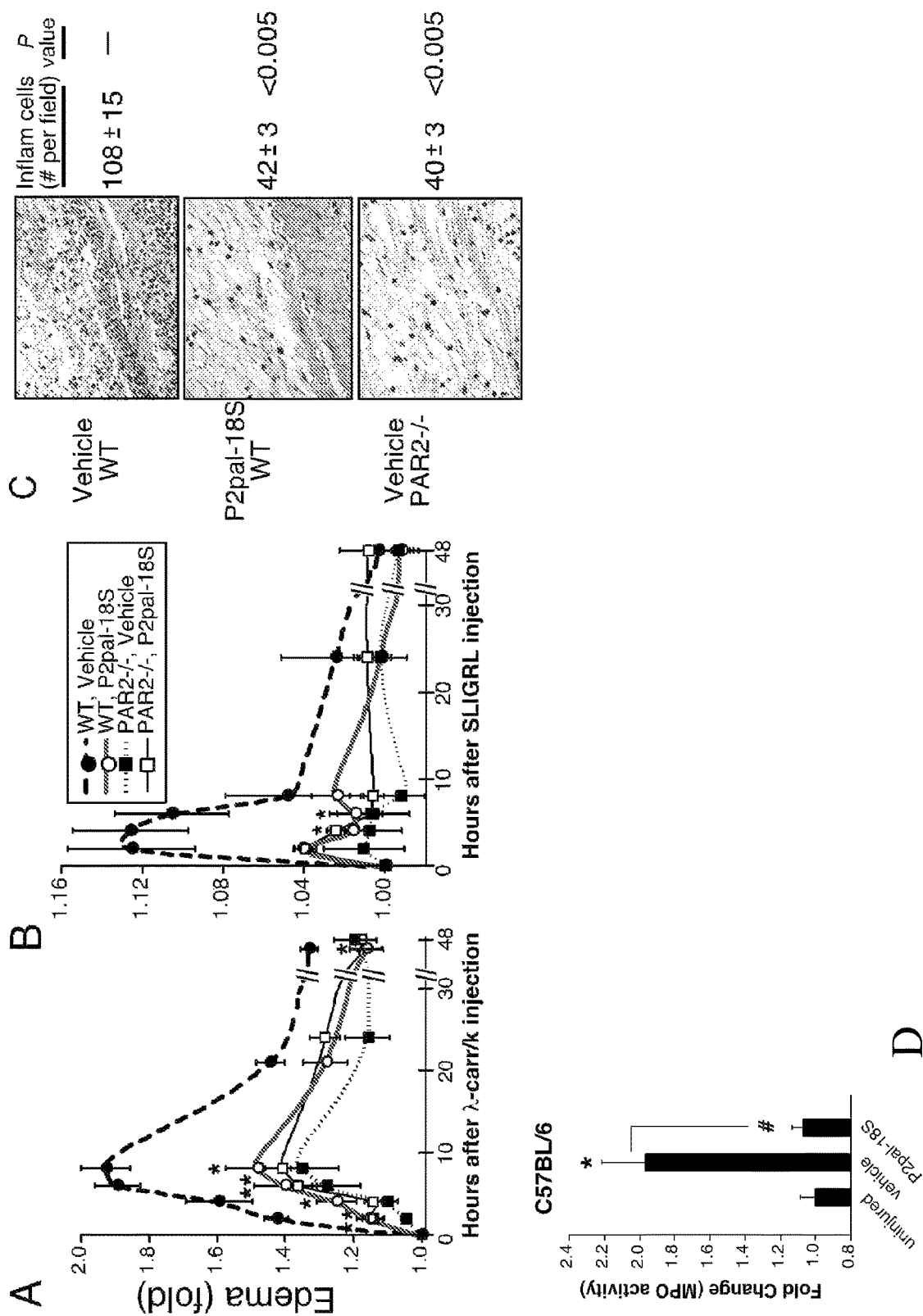

FIG. 6 illustrates that the PAR2 antagonist pepducin P2pal-18S significantly reduces mouse paw edema and inflammation in wild-type but not PAR2-deficient mice. (A) λ-carrageenan/kaolin or (B) the PAR2 specific agonist SLIGRL was administered by intraplantar injection to the left hindpaw of C57BL/6 wild-type or PAR2$^{-/-}$ mice that were treated with subcutaneous (s.c.) injection of 10 mg/kg of P2pal-18S or vehicle. Paw area was measured and reported as fold-increase relative to baseline paw area. (C) Histology of representative H&E-stained footpads 7 h after λ-carrageenan/kaolin injection and quantification of the infiltrating inflammatory cells at 40× magnification. Data (n=4-6/group) mean±SEM. *, P<0.05 and **, P<0.005 (D) Assessment of myeloperoxidase activity in mouse hindpaw tissue 7 h after λ-carrageenan/kaolin injection in mice treated with P2pal-18S (10 mg/kg, s.c., 100 µL) or 20% DMSO vehicle. Data (n=3-5) show the mean±SEM. *, P<0.05 and #, P=0.056.

Figure 7:
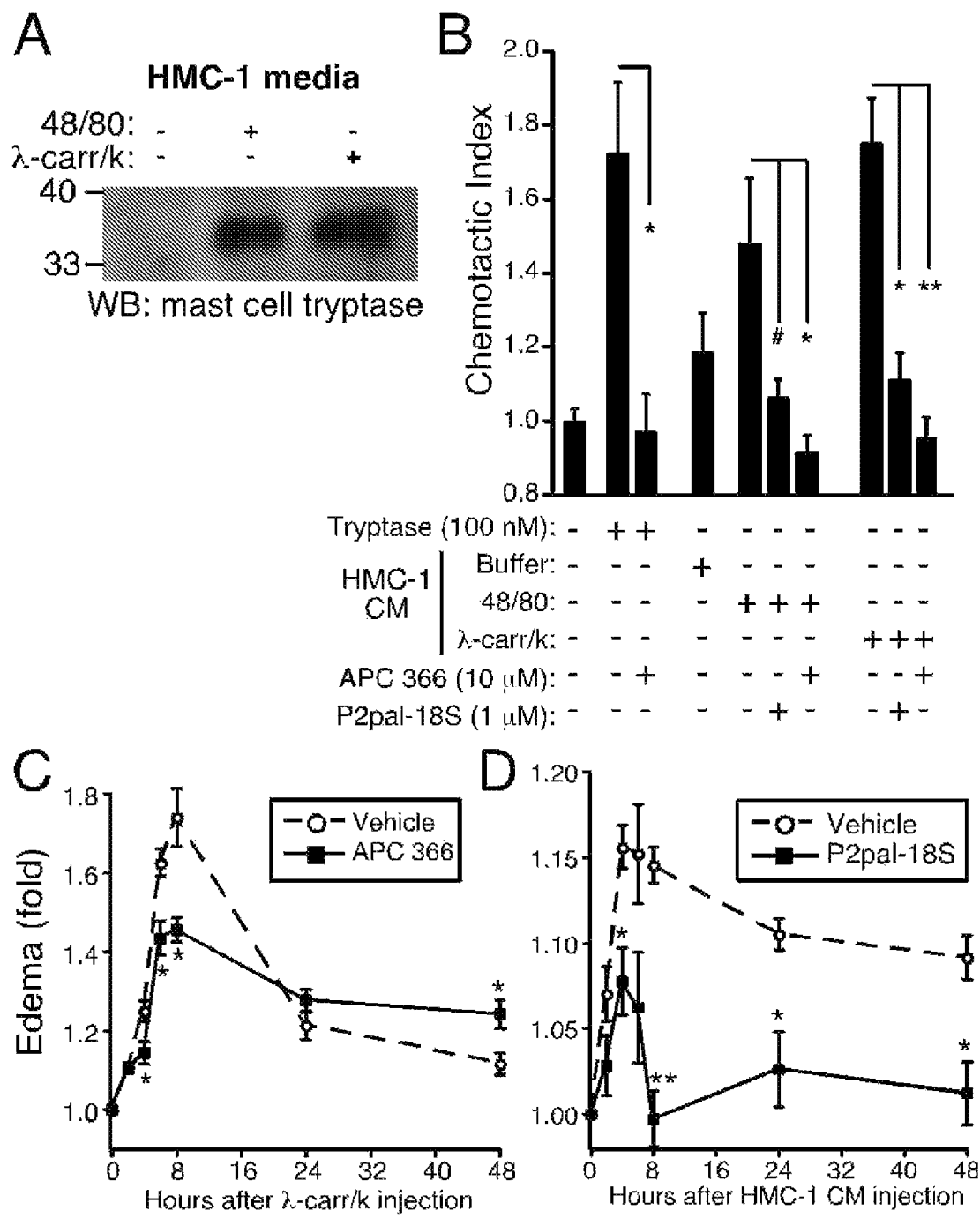

FIG. 7 illustrates that P2pal-18S significantly attenuates mast cell tryptase-dependent neutrophil migration and paw edema in mice. (A) Mast cells were treated with 2 mg/mL of mast cell degranulating agent 48/80 or 2% 1-carrageenan/4% kaolin. Conditioned media (CM) was harvested at 24 h and a western blot of mast cell tryptase shows release of tryptase. (B) P2pal-18S inhibits human neutrophil chemotaxis (n=6) to mast cell media. Human neutrophils were incubated with 1 mM P2pal-18S, or 10 mM mast cell tryptase inhibitor APC-366 and allowed to migrate 30 min toward CM from mast cells. (C) C57BL/6 mice (n=5) were pretreated with the tryptase inhibitor APC-366 (5 mg/kg, s.c.) or vehicle (20% DMSO) and then challenged with intraplantar injection of 1-carrageenan/kaolin. (D) Mast cell conditioned media (30 µL of 1-carrageenan/kaolin stimulated media) was injected into the hindpaws of C57BL/6 mice treated with 10 mg/kg P2pal-18S or vehicle (n=5). Data represent mean±SEM. #, P=0.07, *, P<0.05 and **, P<0.005. (E) Mast cell-deficient mice have a significant reduction in 1-carrageenan/kaolin induced paw edema (8 h time point, n=4-6) as compared to littermate controls. Mast-cell deficient mice or littermate controls with intact mast cells were treated with P2pal-18S (10 mg/kg, s.c.) or vehicle and hind paws challenged with 1-carrageenan/kaolin irritant. Error bars represent mean±SEM.

Figure 8:
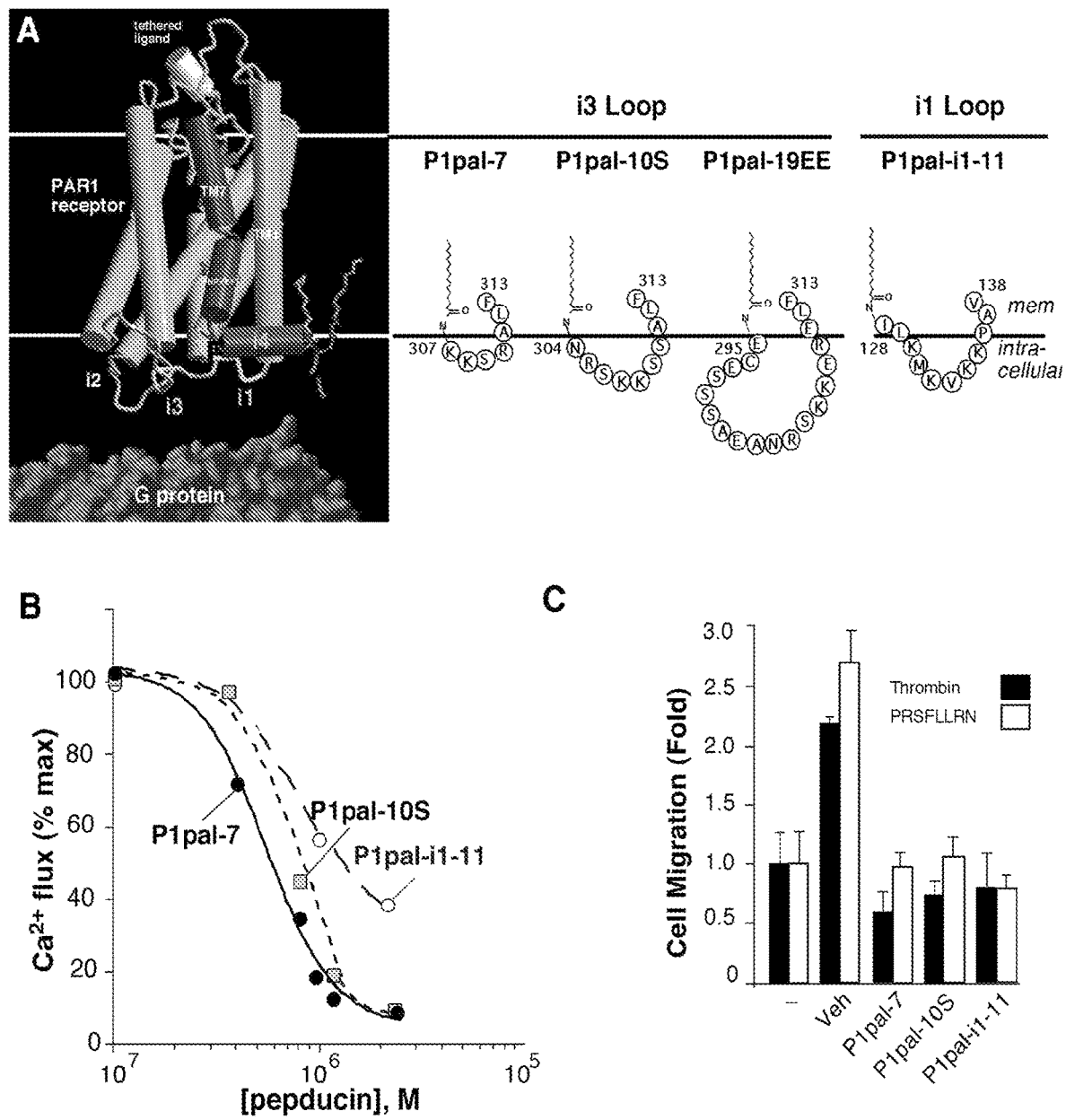

FIG. 8 illustrates data that show membrane-tethered PAR1-i3 and i1 pepducins block Ca$^{2+}$ flux and migration. (A): Model of PAR1 based on the λ-ray structure of rhodopsin from Swift et al., 2006. Protease cleaved receptor results in generation of a new tethered ligand. The topologic arrangement of the it to i4 loops and G proteins are illustrated. Schematic diagram of palmitoylated PAR1 i3 and i1 pepducins and their amino acid sequence composition are shown. (B): Effect of PAR1 pepducins on human platelets Ca$^{2+}$ flux. Platelets were preincubated with indicated concentrations of pepducins and stimulated with SFLLRN. Effect of blockade is expressed as the percentage of full Ca$^{2+}$ signal generated with SFLLRN in the absence of inhibitors. (C): Migration of A549 cells toward 0.3 nmol/L thrombin or 10 µmol/L PRSFLLRN in the presence or absence of 3 µmol/L P1pal-7, P1pal-10S, or P1pal-i1-11 after 18 hours. Basal migration (−), migration of A549 cells toward PAR1 ligand (Veh). Cell migration is expressed as fold migration of ligand-mediated migration divided by basal migration.

Amino acid sequences shown in FIG. 8A are hereby referenced as follows:
P1pal-7: SEQ ID NO:25;
P1pal-10S: SEQ ID NO:26;
P1pal-19EE: SEQ ID NO:27; and
P1pal-i1-11: SEQ ID NO:28.

Figure 9:
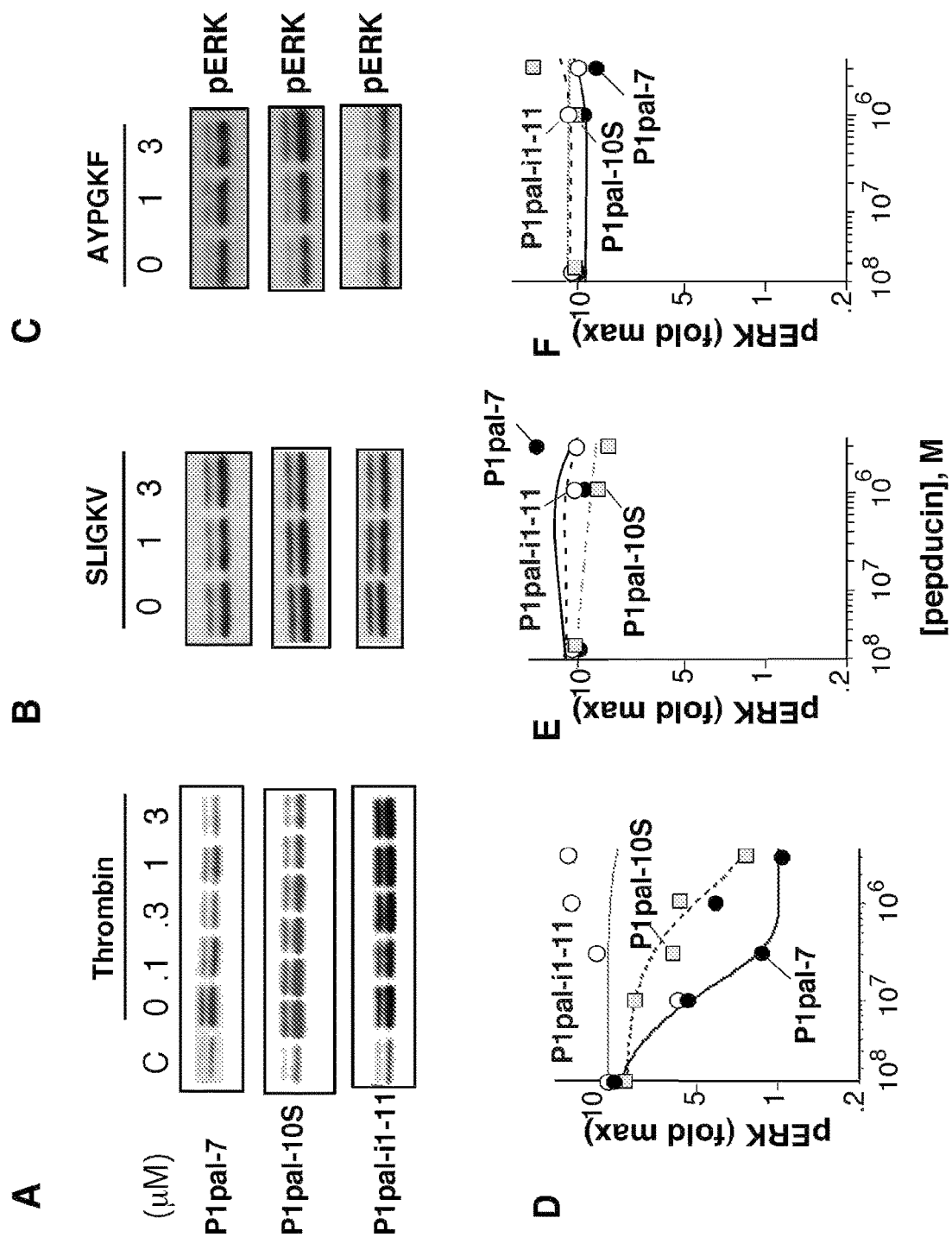

FIG. 9 illustrates that differential inhibition of PAR1-ERK activation by i3- and i1-derived PAR1 pepducins. (A-C): Western blots of lysates from A549 cells untreated, or treated with thrombin, SLIGKV (SEQ ID NO:29), or AYPGKF (SEQ ID NO:5). Indicated samples were pretreated with various concentrations (0.1 to 3 µmol/L) of P1pal-7, P1pal-10S, or P1pal-i1-11 before stimulation and immunoblotted with anti-phospho-ERK. (D-F): Quantification of the Western blots in (A-C) were conducted by densitometry and results are expressed relative to maximum (fold max) phosphorylation of pERK.

FIG. 10 illustrates that P1pal-7 can completely blocks ERK phosphorylation signal: (A): Western blots of lysates from A549 cells stimulated 0.3 nM with thrombin over 2 h and immunobloted with anti-phospho-ERK. (B): A549 cells stimulated with 10 µM PRSFLLRN over 2 h. A549 cells pretreated with 0.1 µM P1pal-7 and stimulated with 10 µM PRSFLLRN (SEQ ID NO:30) for 5 min. Total ERK was used as a loading control.

Figure 11:
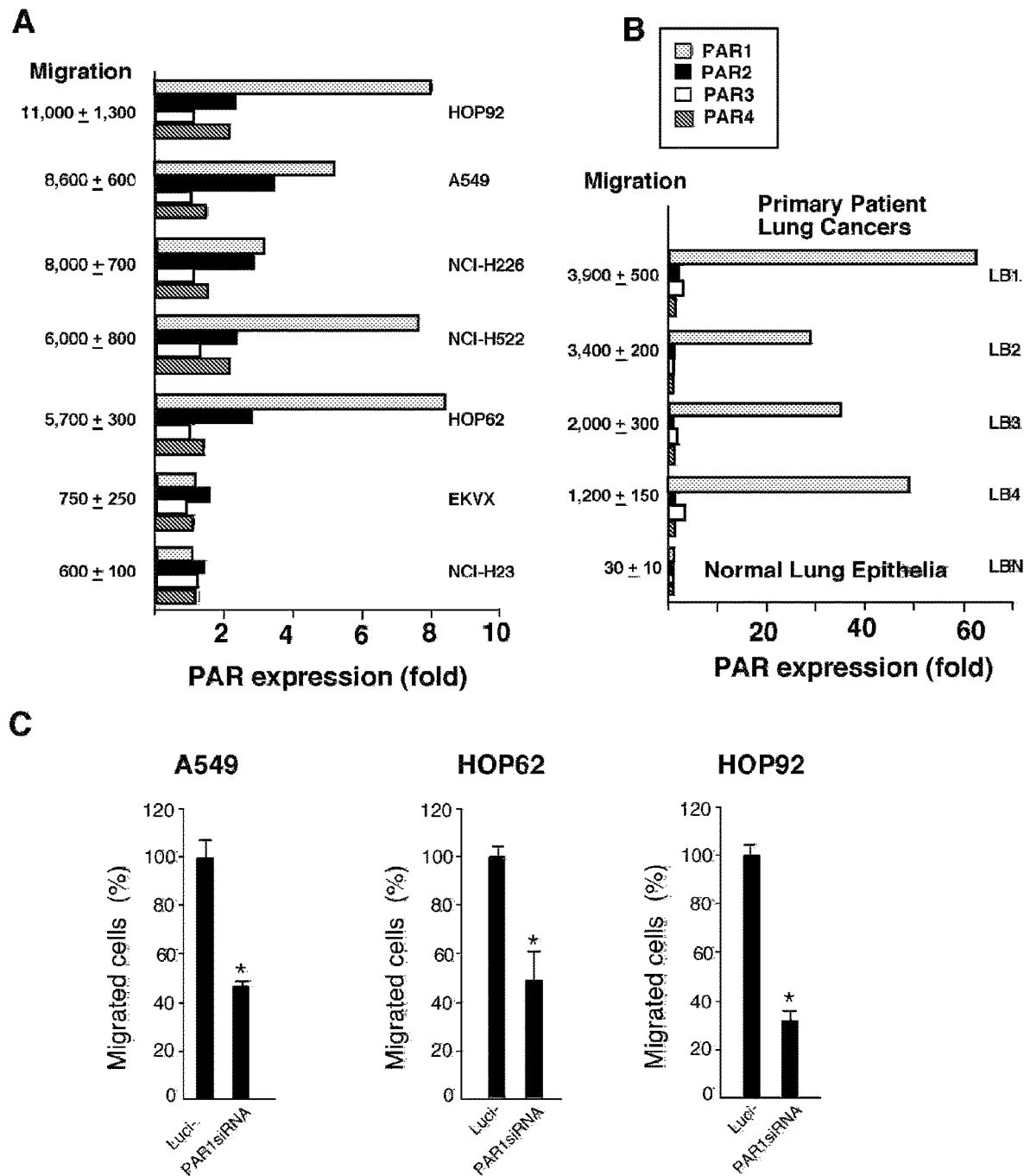

FIG. 11 illustrates PAR expression profile in lung cancer. Lung cancer cell lines (n=7) from the NCI-60 panel were characterized for surface expression of PAR1, PAR2, PAR3, and PAR4 (A) as previously described in Nguyen et al., 2006. (B): PAR mRNA expression profile in patient samples. Quantitative real-time PCR analysis of PAR1 to PAR4 (corrected for actin expression as internal control) and expressed as fold increase over nonmalignant lung tissue. Migration of lung carcinoma cell lines toward fibroblast conditioned media is expressed as cell number ±SD. (C): Silencing of PAR1 expression in A549 and HOP62 cells with shPAR1 or vector control. Surface expression of PAR1 was determined by flow cytometry using SFLLR-Ab. (D):

Migration of A549 and HOP62 lung cancer cells toward NIH-3T3 conditioned media supplemented with RWJ-56110 (10 µmol/L) and SCH7979 (50 µmol/L) or vehicle (0.2% dimethyl sulfoxide). Migration of lung cancer cells treated with shPAR1 treatment or appropriate controls toward NIH-3T3 conditioned media. Basal migration toward conditioned media (vehicle treated or vector control) was normalized to 100%. *P<0.05, **P<0.01.

Figure 12:
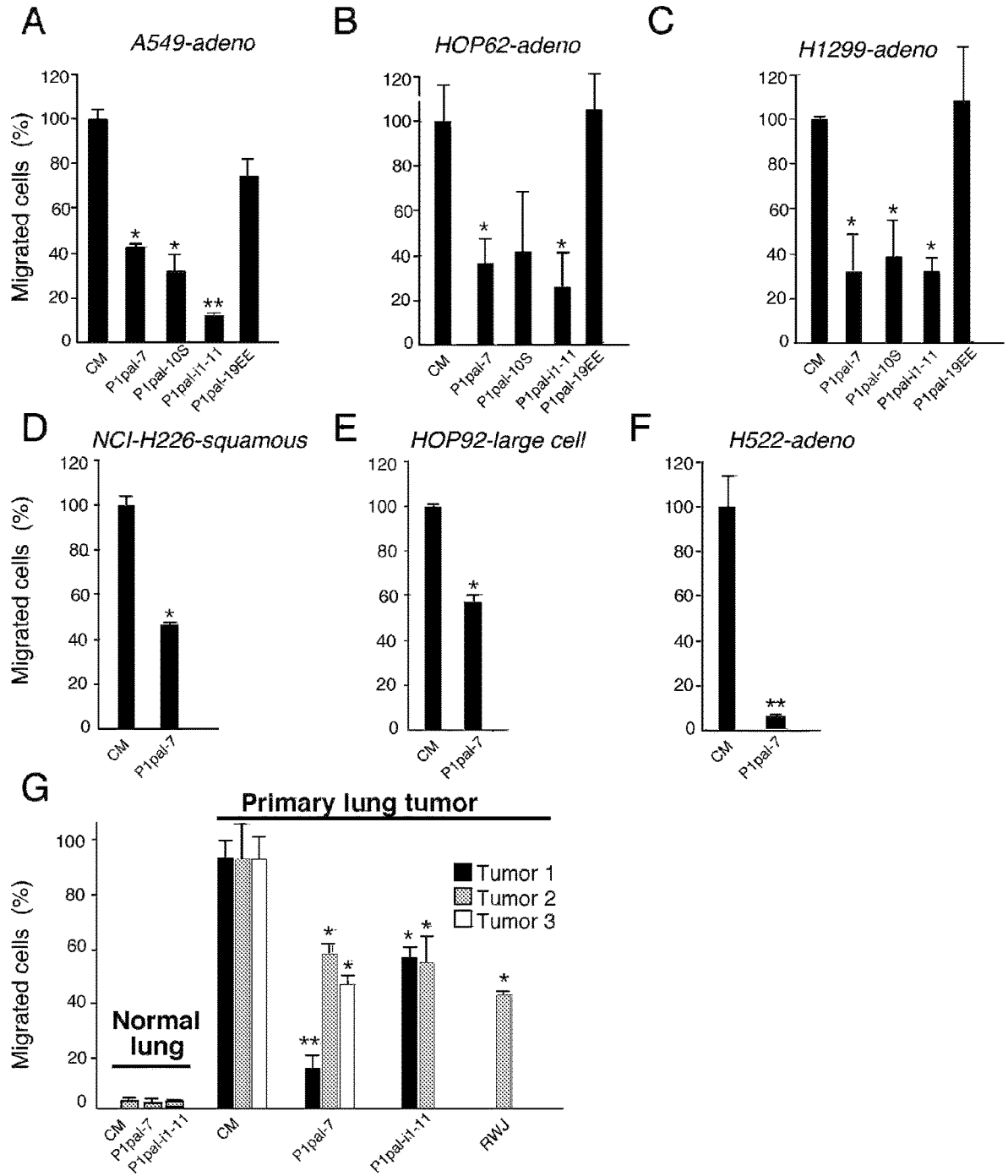

FIG. 12 illustrates that PAR1 is a promigratory factor in lung cancer cells. (A-F): Inhibition of lung cancer migration in adenocarcinomas A549, HOP62, H1299 and H522, H226 squamous, and HOP92 large cell using PAR1 pepducins. Pepducins at 3 mol/L (P1pal-7, P1pal-10S, P1pal-i1-11, or negative control P1pal-19EE) were added to the lower well. (G): Cell from primary lung tumors or nonmalignant control were pretreated with PAR1 pepducins and migration was determined (*P<0.05, **P<0.01).

FIG. 13 illustrates that monotherapy with PAR1-i3 pepducins inhibits tumor progression of A549 xenografts. (A) and (B): A549 mice treated with vehicle, P1pal-7, P1pal-i1-11, P1pal-10S, X1/2-i1, X1/2-i3, or Avastin. Each time point represents the mean±SE. (C): Final tumor volume at the completion of the experiment was calculated as a percentage of untreated vehicle control. (D): Serum-starved A549 adenocarcinoma cells were pretreated with P1pal-7, P1pal-10S, P1pal-i1-11, vehicle, or PD98059 and stimulated with thrombin. VEGF production was assessed by enzyme-linked immunosorbent assay. Data are expressed as mean±SD (*P<0.05, **P<0.01).

FIG. 14 illustrates pharmacokinetics of PAR1 pepducins. (A): CF-1 mice were injected subcutaneously with P1pal-7 (3 mg/kg, open circles), P1pal-7 (10 mg/kg, closed circles), P1pal-10S (10 mg/kg, gray circles), or P1pal-i1-11 (10 mg/kg, open squares) in 20% dimethyl sulfoxide and blood was collected at indicated time points (n=3). Pepducin levels in plasma were quantified with LC/MS/MS. (B): Daily (D1 to D6) plasma levels of P1pal-7 after subcutaneous injection of 10 mg/kg P1pal-7 were measured at 1 hour (open circles) and 24 hours (open squares).

Figure 15:
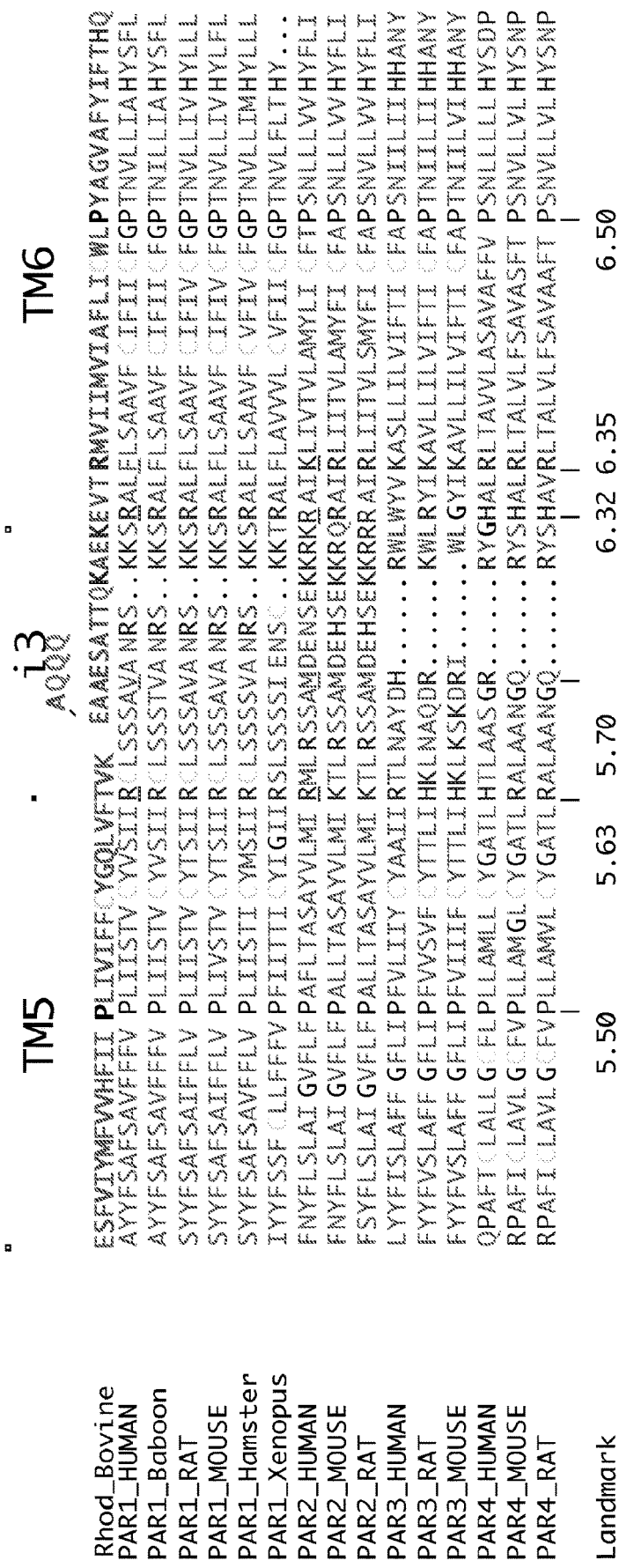

FIG. 15 shows how i3 loop residues can be defined using TM5 and TM6 landmark residues using the Bellesteros system. Amino acid sequences shown in FIG. 15 are hereby referenced as follows:
  Rhod_Bovine: SEQ ID NO:31;
  PAR1_HUMAN: SEQ ID NO:32;
  PAR1_Baboon: SEQ ID NO:33;
  PAR1_RAT: SEQ ID NO:34;
  PAR1_MOUSE: SEQ ID NO:35;
  PAR1_Hamster: SEQ ID NO:36
  PAR1_Xenopus: SEQ ID NO:37;
  PAR2_HUMAN: SEQ ID NO:38;
  PAR2_MOUSE: SEQ ID NO:39;
  PAR2_RAT: SEQ ID NO:40;
  PAR3_HUMAN: SEQ ID NO:41;
  PAR3_RAT: SEQ ID NO:42;
  PAR3_MOUSE: SEQ ID NO:43;
  PAR4_HUMAN: SEQ ID NO:44;
  PAR4_MOUSE: SEQ ID NO:45; and
  PAR4_RAT: SEQ ID NO:46

DETAILED DESCRIPTION

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section shall control.

As used herein, the term "about" or "approximately" when used in conjunction with a number refers to any number within 1, 3, 5, 10 or 15% of the referenced number.

As used herein, "juxtamembrane" means close to the membrane.

As used herein, the term "peptide" or "polypeptide" refers to a molecule composed of monomers (amino acids) linearly linked by amide bonds (also known as peptide bonds). The term "polypeptide" refers to any chain or chains of two or more amino acids, and does not refer to a specific length of the product. A "peptide" or "polypeptide," as used herein, may be derived from a natural biological source or produced by recombinant technology, but is not necessarily translated from a designated nucleic acid sequence. It may be generated in any manner, including by chemical synthesis. One or more of the amino acids in an inventive polypeptide may be modified, for example, by the addition of a chemical entity such as a carbohydrate group, a phosphate group, a farnesyl group, an isofarnesyl group, a fatty acid group, an acyl group (e.g., acetyl group), a linker for conjugation, functionalization, or other known protecting or blocking groups. In a preferred embodiment, the modifications of the peptide lead to a more stable peptide (e.g., greater half-life in vivo).

As used herein, the terms "administration," "administering," or the like, when used in the context of providing a pharmaceutical composition to a subject, generally refers to providing to the subject one or more pharmaceutical compositions comprising an agent in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery.

As used herein, an "agonist" refers to any natural or synthetic molecule or combination of molecules that increases a biological activity by at least or at least about 2 fold, about 3 fold, about 4 fold, about 5 fold, about 7 fold, about 10 fold, about 20 fold, about 50 fold or about 100 fold or more in a standard bioassay or in vivo or when used in a therapeutically effective dose.

An "antagonist" or "inhibitor" may be used interchangeably herein and refers to any natural or synthetic molecule or combination of molecules that interferes with a target's biological activity, depending on the situation, by at least about 30%, about 40%, about 50%, about 60%, about 70%, about 80%, about 85%, about 90%, about 95%, about 98%, or about 100% in a standard bioassay or in vivo or when used in a therapeutically effective dose.

As used herein, to "modulate" means to act as an antagonist, i.e. partially or fully inhibit, reduce, alleviate, block or prevent; or to increase or stimulate, i.e. to act as an agonist. The modulation may be direct or indirect.

The Human PAR family includes PAR-1 (Genbank Accession Number AF019616); PAR2 (Genbank Accession Number XM-003671); PAR3 (Genbank Accession Number NM-0041101); and PAR4 (Genbank Accession Number NM-003950.1), the sequences of which are hereby incorporated by reference.

PAR-1 or protease activated receptor 1 (other aliases: CF2R, HTR 2, PAR1 or TR) is also known in the art as thrombin receptor or coagulation factor II (thrombin) receptor (HGNC: 35371; Entrez Gene: 21492; UniProtKB: P251163; Ensembl: ENSG000001811047). The human PAR-1 polypeptide sequence has Genbank Accession No. NP_001983, which is also incorporated herein by reference and also reproduced in FIG. 9B.

In this disclosure, reference to PAR family members in general or to any individual member of the PAR family member, such as PAR-1, will be understood to refer to all splice variants, mutants (including, but not limited to, deletions, insertions or polymorphisms or amino acid substitutions), isoforms and homologues thereof.

The term, "patient," as used herein, refers to any individual organism. For example, the organism may be a mammal such as a primate (i.e., for example, a human). Further, the organism may be a domesticated animal (i.e., for example, cats, dogs, etc.), livestock (i.e., for example, cattle, horses, pigs, sheep, goats, etc.), or a laboratory animal (i.e., for example, mouse, rabbit, rat, guinea pig, etc.).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pepducin" and "lipopeptide" are cell-penetrating peptides that act as intracellular inhibitors of signal transference from receptors to G proteins. Pepducin lipopeptides utilize lipidated fragments of intracellular G protein-coupled receptor loops to modulate GPCR action in targeted cell-signaling pathways. A pepducin lipopeptide molecule comprises a short peptide derived from a GPCR intracellular loop tethered to a hydrophobic moiety. This structure allows pepducin lipopeptides to anchor in the cell membrane lipid bilayer and target the GPCR/G protein interface via a unique intracellular allosteric mechanism. Examples of pepducin lipopeptides are described in U.S. Patent Publication US2007/0179090, the contents of which are hereby incorporated herein by reference in its entirety.

The term "therapeutically effective amount" as used herein means that amount of active compound or pharmaceutical "agent" that elicits the biological or medicinal response in a tissue, system, animal or human that is being sought by a researcher, veterinarian, medical doctor or other clinician.

As used herein, "treating" or "treatment" cover the treatment of a thrombotic disease-state in a mammal, particularly in a human, and include, but not limited to: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The design of new-generation pepducins that are the subject of the present invention is based on 3D structural models of GPCRs, e.g., a PAR2 dimer, and by mutating one or more amino acid residues that contribute to key pharmacophores in regions of the receptor and analogous pepducins, e.g., in the intracellular loops and neighboring domains. Individual pharmacophores were identified that regulate constitutive agonist and antagonist activities. Novel pepducins derived from disruptions of these pharmacophores were then constructed and they showed specific, and in some embodiments, complete antagonistic effects on their cognate GPCRs. In other words, mutations at these positions can convert an agonistic pepducin that was originally based on the sequence of a wild-type GPCR (or a fragment of the GPCR) into an antagonist that preferably has no substantial agonist functionality. The level at which a candidate pepducin can be considered as having no substantial agonist effect against a target GPCR varies with different GPCRs, and in some embodiments, as measured against a fully functional agonistic counterpart, that level is reached when the wild type agonistic effect is reduced to a physiologically insignificant level, e.g., less than 20%, 15%, 10% or 5% of a measurable variable indicative of agonistic effects such as the calcium flux velocity across cell membranes. With novel pepducin antagonists produced this way, our data further provide evidence they would afford effective treatments of the many diseases and ill conditions that are regulated by GPCRs.

In PAR2, this approach culminated in the identification of the P2pal-18S pepducin (SEQ ID NO:20) which completely suppressed trypsin and mast cell tryptase signaling through PAR2 in neutrophils and colon cancer cells. This PAR2 pepducin, based on mutated versions of PAR2's third (i3) loop and the neighboring sixth transmembrane helix (TM6), was highly efficacious in blocking PAR2-dependent inflammatory responses (e.g., edema). These effects were lost in PAR2-deficient and mast-cell deficient animal models, thereby validating the specificity of the pepducin in vivo. Taken together, the new PAR2 pepducin antagonists provide bases for pharmaceutical compositions for treating and/or preventing debilitating inflammatory diseases and conditions that involve trypsin, tryptase and other protease agonists of PAR2.

In PAR1, another member of the PAR family, mutations at key pharmacophore-contributing positions of PAR1's third (i3) loop produced similarly remarkable pepducin antagonists which showed no substantial agonistic effects and which showed significant inhibition of cell migration in both the primary lung cancer and established cell lines similar to silencing of PAR1 expression with shRNA, and acted as effective inhibitors of PAR1-mediated ERK activation and tumor growth. Comparable in efficacy with Avastin, monotherapy with the novel PAR1 pepducin gave significant 75% inhibition on lung tumor growth in nude mice. With the PAR1-ERK1/2 pathway identified as a valid target in lung cancer therapeutics, novel pepducins that are based on mutated PAR1 or its fragments provide new compositions for pharmaceutical applications against lung cancer and other diseases.

Structural Model and Identification of Critical Pharmacophores

Pepducins are cell-penetrating peptides or polypeptides developed to inhibit GPCRs on the inside surface of the lipid bilayer. First-generation pepducins are derived from the wild-type sequence of their target receptor or its fragments, and are linked to a membrane-associating or penetrating, hydrophobic moiety. In an embodiment, a first-generation pepducin comprises a lipid tether conjugated to the peptidic portion of an intracellular loop of a GPCR, see U.S. Pat. No. 6,864,229. However, it has been extremely difficult to construct an effective antagonist based on existing pepducins while many of their target receptors tend to remain constitutively active. For a decade, various molecular biology techniques had been deployed to try to devise an effective pepducin antagonist against some of the constitutively active receptors but to no avail. For example, random mutations at the i1, i2, i3 and i4 loops of PARs-derived pepducins had not produced satisfactory results, as too many variables existed with mutational positions and length variation.

However, with the advance in high-resolution modeling techniques and programs, the present invention is able to provide compositions and methods for a new generation of rationally designed pepducins that incorporate disruption or change in pharmacophores identified through structural modeling of in vivo configurations of the receptors with or without their associative ligands and/or G-proteins. A pharmacophore, as used herein, describes a molecular feature necessary for molecular recognition of a ligand by a biological macromolecule such as a receptor. A pharmacophore can be a group of steric and electronic features necessary to ensure optimal supramolecular interactions with a specific biological target and to trigger (or block) its biological response, and includes, e.g., whether a molecule is hydrophobic, aromatic, a hydrogen bond acceptor, a hydrogen bond donor, a cation, or an anion.

With mutations disrupting these pharmacophores, a new generation of pepducins was produced where agonist capacities in previous generations of pepducins were greatly reduced and even eliminated while their antagonist capacities enhanced. Briefly, in one embodiment, a model is first constructed based on a likely 3D model of likely receptor-G protein interactions. Then, the interface area is examined and key residues that point sideways towards their partners across the interface are identified. Candidate pepducins are constructed by attaching a hydrophobic second domain to a first domain which includes more or less the GPCR segment most likely responsible for interface contact—in the case of PAR2, for example, a dimer interface appears to involve PAR2's i3 loop most, and to a lesser extent, its neighboring regions including TM6 and TM5. Mutations such as single-base substitutions are engineered using standard biochemistry and molecular biology protocols at or around one or more of the identified key residue positions. Candidate pepducin's antagonistic and agonistic capabilities can then be tested with or without further optimization such as truncation in the N- and/or C-terminals.

Accordingly, several residue positions in the PAR family were identified and confirmed through the present invention as being important for contributing significantly to the receptor functionality. In human PAR2, these positions include the methionine (M) at position 274, arginine (R) at position 284 and lysine (K) at position 287. Disruption through mutation (e.g., single-base substitution) at R284 in human PAR2 yielded most impressive PAR2 antagonist. According to the Ballesteros numbering system, originally described in Ballesteros and Weinstein, *Methods Neurosci* 25:366-428 (1995), which allows comparison of equivalent positions in the GPCR family by referencing to certain landmark residues, R284 in human PAR2 and its equivalents across members of the PAR family are the 18$^{th}$ residues (or 18 residues) N-terminal of the landmark residue 6.50 in the sixth transmembrane helix (TM6) (FIG. 15). Put differently, the same residue position (R284 in human PAR2 and its equivalent across PAR), is in positions corresponding to 248 of bovine rhodopsin when the third intracellular loop (i3 loop) of the PAR is aligned with the i3 loop of bovine rhodopsin. In human PAR1, the key positions discovered through the present invention include the serine (S) at 309, arginine (R) at 310 and alanine (A) at 311.

Example I

Interdicting PAR2-Driven Inflammation with Cell Penetrating Pepducins

Protease-activated receptors (PARs) are a subfamily of seven-transmembrane GPCRs and are activated through cleavage of part of their extracellular domains and act as sensors of extracellular protease gradients, allowing cells to react to the proteolytic microenvironment during tissue remodeling in cancer and a myriad of other processes such as those involved in acute and chronic inflammation. PAR1 to PAR4 are four of the known PARs. They are expressed throughout the human body.

As has been shown with many GPCRs, there is considerable evidence that PARs can interact with each other and form homo- and hetero-dimers, and pepducins are postulated to mimic these dimeric interactions on the intracellular surface of the lipid bilayer (Leger A J, et al. (2006) *Circulation* 113: 1244-1254). Referring now to FIG. 1A, to initiate the design of PAR2 pepducin antagonists, a molecular model of a PAR2 dimer (right panel) was constructed.

First, the model of PAR2 monomer was constructed using the computer program Modeller based on the structure of x-ray bovine rhodopsin (PDB code 1 HZX) as template (Teller D C, et al. (2001) *Biochemistry* 40: 7761-7772). The structure of bovine rhodopsin shares 45% identity with human PAR2. Residues 51-397 of human PAR2 were substituted for residues 1-346 of bovine rhodopsin. The chemical geometry of the model was then refined using Coot and Refmac5.

Then, to construct a model of the receptor dimmer, an initial model was first constructed of the complex between PAR2 and the intact heterotrimeric G-protein based on the structure of opsin in complex with an C-terminal fragment of the G-alpha subunit (PDB code 3DQB) and the structure of the heterotrimeric G-protein transducin (PDB code 1GOT). Stereochemically reasonable positions were used for side chains that were later subjected to molecular dynamics and energy minimization. A series of two-fold symmetric PAR2 dimer models were then manually constructed while maximizing the surface area between the adjacent receptors. Specifically, the models were constructed to permit favorable contacts between the receptor monomers, and to position the G-protein such that regions of G-βγ known to interact with the receptor were in proximity to the second PAR2 molecule. Models were refined using Coot and the molecular graphics figures were generated using PYMOL. Among these, the model that was most consistent with available data regarding interactions between the receptor pair and the G-protein was selected.

N-palmitoylated peptides and PAR1, PAR2, and PAR4 peptide agonists were synthesized with C-terminal amides by standard fmoc solid-phase methods as previously described (Covic et al., *Nat Med* 2002, 8:1161-1165) by the Tufts University Core Facility. Pepducins were purified by C4- or C18-reverse-phase liquid chromatography. Trypsin, bovine pancreas and human mast cell tryptase (Calbiochem) recombinant IL-8 (Peprotech), thrombin (Haematologic Technologies Inc), myo-[$^3$H]-inositol (PerkinElmer), fura-2, AM and fluorescein goat anti-rabbit (Invitrogen), 1-Carrageenan, kaolin, and 48/80 (Sigma-Aldrich), mouse monoclonal (AA1) to Mast Cell Tryptase (abcam, ab2378), APC-366 (ToCris).

To provide functional evidence that one PAR2 receptor can interact with an adjacent PAR2 receptor, a signaling dead PAR2-RQ mutant was constructed by transposing residues at Q172 and R173 located in the critical 'DRY' TM3 motif (FIG. 1A, the second set of sequence labeled as "QR->RQ"). The PAR2-RQ mutant has an intact protease cleavage site and tethered ligand but cannot signal to G proteins. A noncleavable PAR2-R36A mutant was also constructed which retained the ability to fully signal to the SLIGRL ligand, but was not able to be proteolyzed or directly activated by trypsin. Cells expressing PAR2-R36A or PAR2-RQ alone were unable to migrate toward gradients of trypsin or to activate Gq-PLC-β signaling. However, when the two mutant receptors were co-transfected, chemotactic migration and signaling was restored (FIG. 1B), consistent with a mechanism whereby PAR2-RQ can donate its tethered ligand to transactivate PAR2-R36A. To provide direct evidence that PAR2 can form homodimers or oligomers, we showed that myc-tagged PAR2 can stably associate with T7-tagged PAR2 by coimmuno-precipitation (FIG. 1F). These data indicate that PAR2 has the ability to associate with itself within a homodimer or oligomeric complex.

Interestingly, our data indicate that wild-type PAR2 has constitutive activity in the absence of ligand (FIG. 1C). Constitutive signaling has been observed in GPCRs and is often dependent on critical residues located in the C-terminal juxtamembrane region of the i3 loop (Kjelsberg M A et al. (1992), J Biol Chem 267: 1430-1433). Based on our homodimer model shown in FIG. 1A, it was predicted that certain key residues at the dimer interface, which often is in a juxtamembrane region of a GPCR, likely contribute to the GPCR's pharmacophores more than other residues. According to an embodiment of the present invention, it was further predicted that, specifically in the case of PAR2, the i3 loop and its neighboring domains including the TM5 and TM6 domains, are likely crucial for both the constitutive and ligand-triggered activities, as these domains in particular could potentially interact across the PAR2 dimer interface with the 8th helix region from an adjacent i4 domain. Explained in a different way, it was predicted, again, based on the 3D homodimer model of PAR2, that key residues in the sideway protrusion (FIG. 1A, right panel) across the dimmer interface and away from the receptor are critical for its pharmacophores and constitutive activity. Of various residues in the i3 loop and its neighboring domains in human PAR2, it was predicted that, according to the present inventive approach, there are at least three residues instrumental for PAR2's activity: methionine (M) at position 274, arginine (R) at position 284, and lysine (K) at position 287.

The importance of residues at these positions was next tested. Mutation of M274 to alanine (labeled as "M274A") ablated the constitutive signal, whereas mutation of K287 to alanine (labeled as "K287A") had no effect (FIG. 1C). Strikingly, mutation of K287 to phenylalanine (labeled as "K287F") gave larger than 2-fold increase in the constitutive signal (also FIG. 1C). Despite losing its constitutive activity, M274A was able to fully signal in the presence of an agonist (FIG. 1D). Likewise, K287A and K287F were also able to fully signal to agonist (FIG. 1E). Conversely, when the arginine at position 284 is mutated to serine (labeled as "R284S"), the mutant exhibited a loss of constitutive signal and was unable to be activated by even high concentrations of peptide ligand. Similarly, the PAR2ΔH8 mutant, which lacks the 8th helix in the i4 domain (FIG. 1A), was completely signaling-dead to ligand (FIG. 1D). Together, these data indicate that the juxtamembrane residues of the i3 loop and its neighboring domains in PAR2 play critical roles in both constitutive and ligand-dependent activities.

Having identified residues important for the signaling of PAR2, a series of pepducins based on the i3 loop and its neighboring domains were next synthesized to see if GPCR activities would be modulated by engineering mutations at and/or around the critical M274, R284 or K287 residues (FIGS. 2A and B). Best shown in FIG. 2C, according to an aspect of the invention, seven chimeric polypeptides known as pepducins were constructed. Each pepducin had two domains: the first consisting of a mutated fragment of PAR2, and the second attached domain consisting of a naturally or non-naturally occurring hydrophobic moiety giving the polypeptide the ability to penetrate the lipid layer of cell membrane. In the examples shown in FIG. 2C, the first domain of each pepducin is derived from the sequence of a fragment of the wild type PAR2 (P2pal-21) spanning one or more of the TM5, i3 and TM6 regions, regions that we found to play critical roles in both the constitutive and ligand-dependent activities of PAR2. Specifically, the first domain of P2pal-21F is 21 amino acid in length, and the first domains of the other six pepducins range from 14 to 18 amino acids. These domains include sequences corresponding to at least two of the critical PAR2 regions, namely, i3 and TM6.

Still referring to FIG. 2C, in an embodiment of the invention, a mutation, such as a single base substitution, is engineered at one of these critical positions. For example, in both P2pal-21F and P2pal-18F, K287 is replaced by phenylalanine (F); in P2pal-18S and P2pal-18Q, R284 is replaced by serine (S) and glutamine (Q), respectively. In another embodiment of the invention, mutations, such as single amino acid substitutions, are engineered at more than one of these critical positions. For example, in P2pal-18SF, K287 and R284 are replaced by phenylalanine (F) and serine (S), respectively; in P2pal-14GF, K287 and M274 are replaced by phenylalanine (F) and glycine (G), respectively; in P2pal-14GQ, R284 and M274 are replaced by glutamine (Q) and glycine (G), respectively. These and other pepducins were then used to test their abilities to affect PAR2 functionalities.

An initial screening for PAR2 pepducin agonist and antagonist activity was performed using the PAR2-expressing human colorectal adenocarcinoma cell line SW620 and the resulting data are presented in FIG. 2 as follows: The wild-type full-length i3 loop pepducin, P2pal-21 (FIG. 2A), gave a weak agonist signal and lacked significant antagonist activity (about 3% inhibition) when tested against the known PAR2 agonist peptide SLIGRL as assessed by calcium flux (FIG. 2C). Consistent with the gain-of-constitutive activity observed in the PAR2-K287F mutant (see above), the analogous P2pal-21F pepducin (Covic et al. 2002, PNAS 99: 643-48) gave full agonist activity but no antagonist activity in the SW620 cells (FIGS. 2A and C). Deletion of the first three residues (R267, M268 and L269) in the i3 loop domain produced pepducin P2pal-18F (FIG. 2A), which gave a slight decrease in agonist activity at lower concentration, but still was devoid of antagonist activity.

Still referring to FIGS. 2A and 2C, in a preferred embodiment, the P2pal-18S pepducin, which replaces the critical R284 pharmacophore residue with serine (S), turned out to be an highly effective antagonist (77% inhibition) of PAR2 and had no detectable or otherwise significant agonist activity in the calcium flux assay as vehicle alone will give a slight 3% reading. Substitution of the C-terminal K287 of P2pal-18S with phenylalanine (F) to make P2pal-18SF, restored agonist activity of the pepducin. The replacement of R284 with glutamine to make P2pal-18Q, yielded nearly no agonist activity but had partial antagonist activity (29% inhibition). The N-terminally truncated P2pal-14GF, which includes both a M274 to glycine (G) mutation and a K287 to phenylalanine (F) mutation, had no significant agonist or any detectable antagonist activity. However, in a similarly N-terminally truncated pepducin P2pal-14GQ, where R284 was substituted with glutamine (Q) and M274 with G, a gain of 53% antagonist activity was observed and agonist activity remained insignificant or insubstantial.

Based on these data, it appears that, in the i3 loop, the R284 residue holds a powerful position that could significantly boost the antagonist activities of a candidate pepducin construct (see data related to P2pal-18S, P2pal-18SF, P2pal-18Q, P2pal-14GQ which all exhibited significant amount of inhibition of the PAR2 activity, ranging from 29 to 77%). The antagonist effect was particularly pronounced when the arginine residue, which has a relatively long side chain that is positively charged, is substituted with a residue with a shorter side chain such as serine (S). On the other hand, mutating the K287 residue to phenylalanine (F) appears to suppress antagonist activity while enhancing agonist activity (see data related to P2pal-21F, P2pal-18F, P2pal-18SF and P2pal-14GF). When both the R284 to S and K287 to F mutations are present, as is the case of P2pal-18SF, significant amounts of both agonist and antagonist activity are retained. Point mutations at and around M274 also exhibit regulatory effects: the M274 to G mutation (along with N-terminal truncation) appears to offset some of the agonist-boosting ability of the K287 to F mutation when both appear in the P2pal-14GF construct.

From this initial calcium flux screen, the properties of some pepducin embodiments of the invention, e.g., P2pal-18S and P2pal-14GQ antagonist pepducins were further analyzed for their ability to block other PAR2 functions.

a. As Specific Antagonists of PAR2 Activity in Neutrophils

The ability of some pepducin embodiments of the invention to antagonize PAR2-dependent activity of human neutrophils was tested. Neutrophils were isolated from the peripheral blood of healthy human volunteers and found to express high levels of surface PAR2 and PAR4 and lower apparent levels of PAR1 by flow cytometry (FIG. 3A). Neutrophils robustly migrated towards gradients of the PAR2 agonists trypsin and SLIGRL which was completely blocked by P2pal-18S with $IC_{50}$ values of 0.14-0.2 µM (FIG. 3B). Likewise, 0.3 µM P2pal-18S completely blocked chemotactic migration of human neutrophils to 100 nM tryptase (FIG. 3C). As human PAR2 shares 85% identity with mouse PAR2 and the mouse i3 loop retains all of the critical pharmacophores identified in the human PAR2 i3 loop, cross-species inhibition with mouse cells was tested. Indeed, P2pal-18S also completely inhibited the migration of mouse neutrophils toward 30 nM trypsin (FIG. 3D).

Specificity of P2pal-18S for PAR2 was evident as it had no antagonist activity to the closely related PAR1, PAR4, or CXCR1/2 IL-8 receptors in neutrophil chemotaxis assays (FIG. 3E). P2pal-18S did not inhibit PAR1 or PAR4 by calcium flux assays in SW620 cells, nor in inositol phosphate signaling in COS7 cells, despite providing effective inhibition to the PAR2 ligand SLIGRL (FIGS. 4A and 4B). The P2pal-14GQ pepducin was also selective for PAR2 and not PAR1, but was not as efficacious in suppressing migration of SW620 cells to SLIGRL as compared to P2pal-18S (FIGS. 4A-4C). P2pal-18S had no effect on PAR1-dependent platelet aggregation (FIG. 5A). Neither P2pal-18S nor P2pal-14GQ caused membrane disruption or apoptosis as assessed by propidium iodide uptake in SW620 cells with up to 30 µM concentrations of pepducin (FIG. 5B).

It was also found that P2pal-18S blocked transactivation of PAR2-homodimers as shown by complete suppression of chemotactic migration of HEK cells co-expressing PAR2-R36A and PAR2-RQ mutants (FIG. 4D). Furthermore, as evidence that the P2pal-18S peptide directly interacts with PAR2, PAR2 had enhanced binding to avidin beads coupled with the PAR2 i3 loop 18S peptide as compared to beads alone. Additionally, we tested whether P2pal-18S inhibited proteolytic cleavage of PAR2 or endocytosis (DeFea K A, et al. (2000) *J Cell Biol* 148: 1267-81; Roosterman D, et al. (2003) *Am J Physiol Cell Physiol* 284: C1319-29; Stalheim L, et al. (2005) *Mol Pharmacol* 67: 78-87). P2pal-18S had no effect on trypsin cleavage of PAR2, and did not inhibit ligand-dependent endocytosis of PAR2 or PAR1. Therefore, the P2pal-18S i3 loop pepducin can inhibit PAR2-dependent calcium signaling, PLC-b inositol phosphate formation, and cell migration, but not proteolytic cleavage or endocytosis.

b. Efficacy in Mouse Models of Inflammatory Paw Edema

To evaluate the in vivo efficacy and specificity of P2pal-18S, the ability of the pepducins of the present invention was tested to protect against inflammatory hindlimb paw edema in wild-type (WT) and PAR2-deficient mouse strains (Damiano B P, et al. (1999) *J Pharmacol Exp Ther* 288: 671-78.) Acute inflammatory edema was induced by an intraplantar injection of λ-carrageenan and kaolin, irritants which cause a massive leukocytosis and hyperemic response, which leads to localized swelling. PAR2-dependent activity of an embodiment of the present invention, polypeptide P2pal-18S, was directly assessed by quantifying its inhibitory effects against the PAR2-specific agonist SLIGRL when injected into the hind footpad of WT C57BL/6 mice. Acute inflammation induced by λ-carrageenan/kaolin resulted in a nearly 2-fold increase in paw edema with vehicle-treated WT mice, peaking 8 h after injection (FIG. 6A). The PAR2 agonist peptide, SLIGRL, also induced an increase in edema of WT mice, peaking 4 h after injection (FIG. 6B). Systemic administration of P2pal-18S caused a significant 50% decrease in λ-carrageenan/kaolin-induced edema and an 85% decrease in SLIGRL-induced edema (FIGS. 6A and 6B). PAR2 deficiency conferred a 50% protective effect relative to WT mice following λ-carrageenan/kaolin injection which was nearly identical to the protective effect observed in WT mice treated with P2pal-18S. Notably, treatment of PAR2-deficient (PART) mice with P2pal-18S did not further reduce swelling confirming that the anti-inflammatory effects of the PAR2 pepducin required the presence of its cognate receptor.

Histologic analysis of the inflamed footpads harvested 7 h post λ-carrageenan/kaolin injection revealed that P2pal-18S provided significant 60% protection (P<0.005) against the leukocytic infiltrates in the dermis of the footpads, which was identical to the protection observed in PAR2$^{-/-}$ mice relative to WT mice (FIG. 6C). The λ-carrageenan/kaolin challenge caused a 2-fold increase in myeloperoxidase activity in WT mice, which was blocked by P2pal-18S (FIG. 6D). Together, these data demonstrate that the PAR2 pepducin P2pal-18S affords significant protection against acute leukocytic inflammation and edema and these protective effects are dependent on the presence of PAR2.

c. Protection Against Mast Cell Tryptase-Induced Inflammation

Previous studies have established that mast cell tryptase cleaves and activates PAR2 signaling in human endothelium and keratinocytes and in mouse models of arthritis (Kelso E B, et al. (2006) *J Pharmacol Exp Ther* 316: 1017-24; Palmer H S, et al. (2007) *Arthritis Rheum* 56: 3532-40). To determine whether mast cells and mast cell tryptase were contributing to the observed PAR2-dependent effects in the mouse models of paw inflammation, mast cells were stimulated with the degranulating agent 48/80, or λ-carrageenan/ kaolin and collected conditioned media. As shown in FIG. 7A, the stimulated mast cells secreted tryptase which was then used as a chemoattractant source in neutrophil chemotaxis assays. The conditioned media from the stimulated mast cells gave comparable chemotactic migration as 100 nM tryptase (FIG. 7B). Treatment of human neutrophils with tryptase inhibitor, APC-366, or the PAR2 pepducin P2pal- 18S, completely inhibited chemotactic migration toward the tryptase-containing mast cell media (FIG. 7B).

Figure 7E:
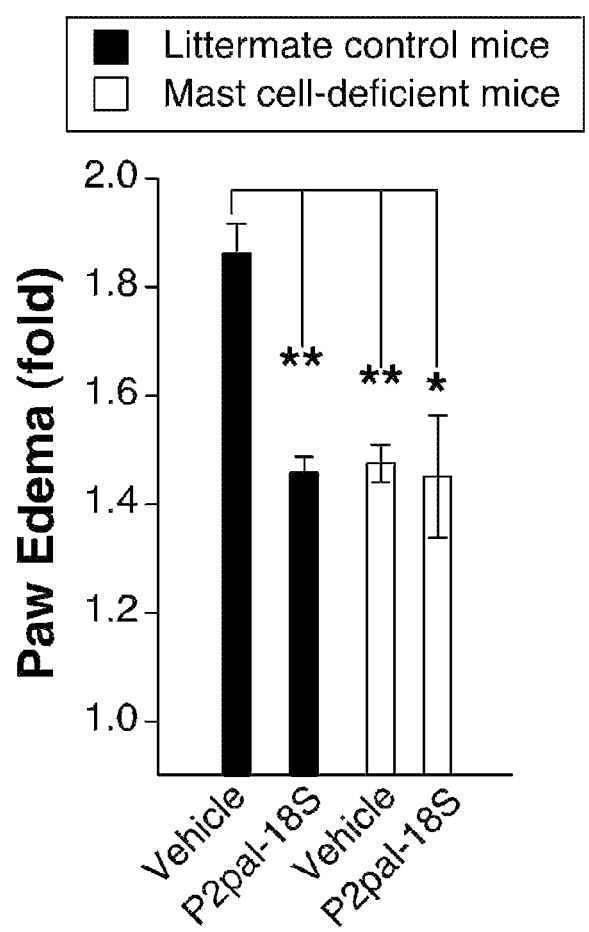

To examine whether mast cells and mast cell tryptase were activating PAR2 in the paw edema model in vivo, mice were depleted of mast cells through pretreatment with compound 48/80 (Carvalho M et al. *Eur J Pharmacol* (2005), 525: 161-169). A decrease in λ-carrageenan/kaolin-induced edema in the 48/80-depleted animals was observed as compared to non-treated controls. Similarly, mice treated with tryptase inhibitor APC-366, gave a significant 40% protection in λ-carrageenan/kaolin-induced paw edema (FIG. 7C). An intraplantar injection of the tryptase-containing mast cell media resulted in a similar peak increase in paw edema (FIG. 7D) as induced by the selective PAR2 agonist SLIGRL (FIG. 6B). Systemic treatment with P2pal-18S gave a 50% decrease in peak development of edema at 4 h and afforded complete protection at 8 h and thereafter (FIG. 7D). To provide further evidence that mast cell-derived tryptase mediates the observed PAR2-dependent inflammatory responses, we then challenged mast cell-deficient mice with λ-carrageenan/kaolin and observed that these mice had an identical, reduced-paw-edema response as P2pal-18S-treated littermate control mice that have intact mast cells (FIG. 7E). Furthermore, the observed paw edema in the mast cell-deficient mice could not be further reduced by treatment with P2pal-18S (FIG. 7E). Together, these data suggest that the P2pal-18S pepducin provides significant protection against inflammatory edema triggered by mast cell-derived tryptase.

The above example describes the development of first-in-class lipopeptide pepducin full antagonists of PAR2. Pepducins are an emerging new technology to target recalcitrant transmembrane receptors such as PAR2. These highly stable lipidated peptides are targeted to the intracellular surface of their cognate GPCR and stabilize the receptor in either an active or inactive conformation, resulting in modulation of signal transduction. Pepducins typically comprise two components: a short peptide sequence derived from an i1-i4 intracellular loop of the target GPCR, and an acyl-chain fatty acid (e.g. palmitate) or other lipid conjugated to the peptide. The rational design of the i3 loop agonist and antagonist pepducins was based on a structural model of a PAR2 dimer and by manipulating key residues in the receptor loops and analogous pepducins after individual pharmacophores that controlled constitutive, agonist and antagonist activities were identified. The most potent pepducin antagonist, P2pal-18S, fully ablated PAR2 signaling but did not inhibit the closely related PAR1 or PAR4 receptors, nor other tested GPCRs.

The PAR2 pepducin antagonist had significant in vivo efficacy in suppressing leukocytic infiltration and edema induced by λ-carrageenan/kaolin or a PAR2-selective agonist in mouse paw inflammation models. The anti-inflammatory effect of the P2pal-18S pepducin was lost in PAR2-deficient mice demonstrating that the pepducin was highly specific for PAR2 in vivo. Moreover, the anti-inflammatory effect observed in the PAR2-deficient mice relative to wild type was nearly identical to that observed in wild-type mice treated with P2pal-18S. Together, these data indicate that P2pal-18S affords effective pharmacologic blockade of PAR2 in models of acute inflammation and that these effects require the presence of PAR2.

Many studies have implicated PAR2 as playing critical roles in a wide range of diseases including asthma (Schmidlin et al., *J Immunol* 2002, 169: 5315-5321), arthritis (Ferrell et al., 2010), hyperalgesia (Vergnolle et al., 2001), neurogenic and cancer pain (Lam et al., 2010), and cancer invasion (Shi et al., *Mol Cancer Res* 2004, 2: 395-402). Several lines of evidence are provided here that the inflammatory response observed in the mouse footpad model was largely dependent on mast cells and mast cell-derived tryptase, an important agonist of PAR2-driven inflammation. We found that the PAR2 pepducin could completely suppress tryptase signaling through PAR2. Moreover, mast cell-deficient mice had an identical reduced paw edema response as P2pal-18S treated littermate controls which had intact mast cells. Furthermore, the paw edema in the mast cell-deficient mice could not be further reduced by treatment with P2pal-18S, providing further support for the notion that mast cell-derived tryptase mediates the PAR2-dependent inflammatory responses in this acute inflammation model. It is possible that the PAR2 pepducin may inhibit signaling induced by other PAR2 protease agonists present in the inflammatory milieu in addition to tryptase.

Two other groups have disclosed PAR2 antagonists based on the tethered peptide ligand (Kelso et al, 2006; Kanke et al., *Br J Pharmacol* 2009, 158: 361-371). In Kelso et al., a PAR2 small molecule inhibitor, ENMD-1068, was tested in a model of joint inflammation. ENMD-1068 requires millimolar concentrations to observe its protective effects in vitro and considerably higher doses in vivo. The peptide antagonist K-14585 was shown to inhibit PAR2-dependent IL-8 production, NF-κB phosphorylation, and p38 signaling (Goh et al., 2009). However, the K-14585 compound has partial agonist activity (Goh et al., 2009; Kanke et al., 2009) as also observed with the wild-type PAR2 pepducin P2pal-21 (Covic et al., 2002). In this regard, the inventors discovered that wild-type PAR2 has constitutive activity indicating that certain extracellular or intracellular PAR2 ligands might stabilize the latent on-state. The realization that constitutive activity could be ablated or enhanced by mutation of critical i3 loop pharmacophores in the intact receptor led the inventors to rationally design PAR2 pepducin antagonists that lost residual agonist activity. The pepducin antagonists thus designed and constructed against difficult GPCR targets such as PAR2 provided novel pharmacological agents in a wide range of diseases that implicates PAR2 signaling, including many involving inflammatory reactions.

Example II

Targeting PAR1-G Protein Signaling and Diseases with New Pepducin

Lung cancer is the leading cause of cancer deaths in the United States and worldwide and is the second most common cancer overall. The majority of patients eventually develop distant metastases which leads to substantial morbidity and mortality. Currently available chemotherapeutic regimens for the treatment of non-small-cell lung cancer (NSCLC) include combinations of cisplatin or carboplatin, and etoposide, paclitaxel, docetaxel, gemcitabine, vinorelbin and irinotecan. These regimens are generally not curative and may confer modest prolongation of life and symptomatic relief. More recently, targeted therapies have become available for the treatment of lung cancer. These include small molecules and antibodies that target epidermal growth factor receptor (EGFR) and vascular endothelial growth factor receptor (VEGFR). However, the currently available molecular therapies still result in relatively modest prolongation of median and overall survival, pointing to the necessity for developing more effective treatment modalities for patients with advanced NSCLC.

Emerging evidence has identified PAR1 as a promising target to impact tumor progression, metastasis and angiogenesis in variety of cancers including breast, ovarian, melanoma, prostate and colon cancer (e.g. Nguyen et al. *Cancer Res* 2006, 66:2658-65). However, the role of PAR1 and the other PAR family members in lung cancer is largely unexplored.

In the present invention, PAR1 was identified as therapeutic target in lung cancer by employing cell-penetrating pepducins generated from the first (i1) intracellular and third (i3) intracellular-loops of PAR1. Pepducin technology was developed to target receptor G-protein interactions at the interface of the plasma membrane. Palmitoylation or use of other lipid moieties attached to the peptide partitions the lipopetide across the plasma membrane and rapidly delivers pepducin to the intracellular surface by flipping across the bilayer. Multiple studies have been carried out to determine the specificity of pepducins to their cognate receptors. In the present invention, PAR1 pepducins based on the i2 and i3-loops had comparable efficacy in inhibiting migration and $Ca^{++}$ signaling. In contrast, i3-targeted pepducins were also found to block PAR1-dependent ERK1/2 activity and VEGF secretion. Monotherapy with i3-based pepducins was more efficacious than with i1-based pepducins and PAR1 inhibited with i3 pepducins significantly inhibited lung tumor growth by up to 75% in xenograft models, similar in efficacy to Avastin. These data identify PAR1 as a new therapeutic target in lung cancer and show that pepducins based on i1 and i3 intracellular loops of PAR1 can block different signaling pathways.

To guide in the design of i1 and i3 pepducins, a model of PAR1 based on the x-ray structure of rhodopsin was generated (Swift et al. *J Biol Chem* 2006, 281:4109-16) as shown in FIG. 8A. As different PAR1 intracellular loops were predicted to interact with distinct regions of the heterotrimeric $G_q$, $G_i$ and $G_{12/13}$ proteins, it was tested whether intracellular blockade of i1 versus i3 loops would preferentially affect different signaling pathways based on the 3D model.

Pepducins where the PAR1-derived first domains contain mutations at key amino acid positions were also constructed for the tests. One of the key amino acids identified through modeling as likely critical for G-protein activation is arginine (R) at position 310 on the i3 loop. In P1pal-10S, R310 is substituted with serine (S) (FIG. 8A). Disruption of R310, e.g., by substituting it with a serine (S) or glutamic acid (E), causes a PAR1 receptor to lose substantially all of its agonistic ability to activate G protein (data not shown), and therefore, is employed here. 3D modeling also shows that residue 309's side chain points directly out towards a partner PAR1, and residue 311's side chain is in the membrane environment. It was contemplated that mutating the residues at these two positions with a charged amino acid glutamic acid would likely disrupt any agonistic functionality. Accordingly, another mutant pepducin, P1pal-19EE was constructed with point mutations in its 19-residue PAR1-derived first domain: substitution of S309 with glutamic acid (E) and A311 with E (FIG. 8A). P1pal-19EE was used in various tests as a negative control. P1pal-10S, with 10 amino acids in its PAR1-derived first domain, was tested as a candidate along with other pepducin candidates, including P1pal-7 which contains seven amino acids in sequence identical to a fragment of the wild type i3 loop in PAR1. Specifically, we tested the efficacy of the i3-loop P1pal-7, the i3-loop P1pal-10S, and the i1-loop P1pal-i1-11 for their ability to block PAR1-mediated $Ca^{++}$ signaling, cell migration and MAP kinase signaling because these are regulated by different signaling pathways.

First, it had been previously shown that PAR1 strongly couples to $G_q$ in human platelets as assessed by $Ca^{++}$ signaling. In order to determine effect of i1 and i3 pepducins on PAR1 mediated $G_q$-PLCβ-InsP$_3$ signaling, human platelets were pretreated with PAR1 pepducins and stimulated with SFLLRN, before the rate of $Ca^{++}$ flux was measured. As shown in FIG. 8B, P1pal-7, P1pal-10S and P1pal-i1-11 effectively inhibited PAR1-dependent $Ca^{++}$ mobilization by SFLLRN with $IC_{50}$ values of 0.55±0.04, 0.70±0.17, and 1.3±0.1 µM, respectively. However, unlike the i3-derived pepducin which could completely inhibit calcium moblization, the i1-derived P1pal-i1-11 was less effective in inhibiting the $G_q$ mediated calcium signal.

Second, through a Boyden chamber migration assay, it was shown that both thrombin and the MMP-1 tethered PAR1-ligand peptide, PRSFLLRN (SEQ ID NO:30), induced migration of A549 lung carcinoma cells (from Developmental Therapeutics, National Cancer Institute/NIH) with a similar magnitude (FIG. 8C). Next, it was examined whether the PAR1 antagonist pepducins of the invention could block migration of the A549 lung adenocarcinoma cells. As demonstrated in FIG. 8C, there was a complete blockade of migration of A549 cells by either i1- and i3-derived pepducins.

Last, there has been a great deal of interest in understanding the mechanism of PAR1-mediated activation of MAP kinase cascade and PAR1-dependent cellular growth and differentiation, proliferation and gene transcription. ERK1/2 activation has been shown to be activated through both $G_i$(βγ)-PI3-kinase and $G_q$ pathways. The effects of i1 versus i3 PAR1 pepducins on ERK1/2 activation were examined in the A549 lung adenocarcinoma cell line. Treatment of A549 cells with thrombin resulted in a rapid and robust ERK1/2 phosphorylation that peaked at 15-30 min after stimulation. Inhibition experiments with a range of pepducin concentrations (0.1-3 µM) were conducted. There was complete inhibition of thrombin-induced ERK1/2 phosphorylation with the i3-derived pepducins, P1pal-7 and P1pal-10S with $IC_{50}$ values of 0.2±0.1 and 0.8±0.2 µM, whereas the i1-derived P1pal-i1-11 had no effect on the phosphorylation of ERK1/2 (FIGS. 9A and 9D). The PRSFLLRN (SEQ ID NO:30) peptide gave a rapid and transient ERK1/2 phosphorylation signal that peaked at 5-15 min after stimulation. Similar to thrombin, 0.1 µM P1pal-7 could completely block the PRSFLLRN-induced phospho-ERK signal (FIG. 10). This indicates that, unlike i1-pepducins, the i3-loop pepducins are effective inhibitors of PAR1-mediated ERK activation. To determine the specificity of the PAR1 pepducin inhibitors, their effects on the closely related PAR2 and PAR4 receptors were also tested. All three PAR1 pepducins were selective for PAR1 and did not cross-inhibit PAR2 nor PAR4 at 1-3 µM concentrations (FIGS. 9B, 9C, 9E, and 9F).

PAR1 Expression is Increased in Highly Aggressive Lung Cancer Cell Lines

A previous histologic analysis suggested that protease-activated receptors PAR1 and PAR4 may have a negative prognostic predictive value on outcome from a study of 60 NSCLC patients, including 30 adenocarcinomas and 30 squamous cell carcinomas (Ghio et al. 2006). Therefore, surface expression of all four PAR members was determined in seven different National Cancer Institute (NCI)-lung cancer cell lines that consisted of five adenocarcinomas, a squamous-cell carcinoma, and a large cell carcinoma using flow cytometry. Of the four PAR family members, PAR1 expression was increased three-fold to nine-fold in the majority of the lung carcinomas, with maximum expression detected in the adenocarcinomas. In contrast, there was only a modest increase of the three other PARs including PAR4 (FIG. 11A). High PAR1-expressing cells showed a 7- to 18-fold higher rate of migration towards conditioned media than the two low-expressing PAR1 cell lines (EKVX and NCI-H23).

To validate the expression of PARs in primary tumor specimens, the mRNA levels were measured using quantitative PCR in five lung specimens isolated from patients who underwent thoracotomy. Based on histopathology, the primary tumors included two adenocarcinomas, one poorly differentiated NSCLC, one squamous carcinoma, and one benign lung specimen. As shown in FIG. 11B, patient lung carcinomas had high levels of PAR1 mRNA and low levels of PAR2, PAR3, and PAR4 mRNA. As was observed with the NCI lung carcinomas, high PAR1 expression in the patient tumors also was accompanied with a large 10- to 40-fold increase in migration of all four primary lung tumor cells as compared with the normal lung tissue.

To further validate the role of PAR1 in lung cancer cell motility, effect of silencing PAR1 gene expression was tested using PAR1 short hairpin RNA in two high PAR1-expressing adenocarcinomas, A549 and HOP62. PAR1 short hairpin RNA silenced the majority of the PAR1 expression in both cell lines (80%±5% and 90%±5%) (FIG. 11C). Next, effect of PAR1 loss on cellular migration was tested using a Boyden chamber migration assay. PAR1 knockdown was found to suppress migration by 55%±5% in A549 cells toward NIH-3T3 conditioned media, and by 80%±5% in HOP62 cells after long-term puromycin selection of shPAR1 and the vector control-treated cells (FIG. 11D).

Because A549 was the cell line that was characterized further in all subsequent in vitro and in vivo experiments, effect of the PAR1 antagonists was also tested on extracellular ligand RWJ-56110 (10 μmol/L) and SCH7979 (50 μmol/L), and 40% to 50% inhibition was found in migration (FIG. 11D). These data are consistent with our previous findings (Nguyen et al, 2006; Agarwal et al., 2008; Yang et al, 2009) that silencing of PAR1 in breast cancer cells is associated with decreased migration.

PAR1 i1 and i3 Pepducins Inhibit Migration of Lung Carcinomas

Given that silencing of PAR1 expression decreased migration, it was further tested whether i1 and i3 PAPA antagonist pepducins would have similar effects on migration of the four NCI lung cell adenocarcinomas (A549, HOP62, H522, and H1299), one large cell (HOP92), one squamous carcinoma (H226), along with three primary patient tumors that consisted of two adenocarcinomas, one poorly differentiated NSCLC, and one normal lung epithelia. Migration of the PAR1-expressing adenocarcinomas were suppressed by 60% to 80% by all three pepducins (FIGS. 12A-C) which was highly similar to the effects seen earlier by PAR1 short hairpin RNA treatment. The negative control PAR1 i3 pepducin P1pal-19EE, had no effect on migration. P1pal-7 provided 40% to 90% inhibition with H226 squamous, HOP92 large cell carcinoma, and H522 adenocarcinoma (FIGS. 12D-F), providing further support that PAPA signaling plays an important role in lung cancer cell migration.

It was further tested whether the PAR1 antagonist pepducins could confer cytotoxicity to lung carcinoma cells using MIT assay, and it was found that pretreatment of A549, H1299, or HOP62 with pertussis toxin, which inactivates iii, results in similar inhibition of migration as PAR1 blockade. Exposure of A549, HOP62, and HOP92 lung carcinoma cell lines to 3 union pepducins over the 5-hour period of cell migration had no significant effects on cell viability. However, over a 3-day period, A549 cells were most sensitive to the i3-derived P1pal-10S and P1pal-7 pepducins and less sensitive to the i1-derived P1 pal-i1-11.

Further experiments were carried out to determine whether migration of the primary carcinoma cell lines isolated from lung tumors could be inhibited by PAR1 pepducins (FIG. 12G). PAR1 pepducins significantly inhibited migration (40% to 80%) of primary lung tumors with comparable efficacy using either P1pal-7 (i3)- or the P1pal-i1-11. Likewise, the RWJ-56110 small-molecule antagonist of PAR1 (Andrade-Gordon, et al., Proc. Natl Acad Sci USA, 96 (1999), pp. 12257-12262) suppressed up to 55% of the migration of primary lung tumor cells toward NIH-3T3 conditioned media. The PAR1 antagonist pepducin P1pal-7 and P1pal-i1-11 had no effect on the low-expressing PAR1 cell line derived from benign lung tissue, which migrated poorly (FIG. 12G). Together, these results suggest that PAR1 is an important contributor migration in lung carcinoma cells and pepducin antagonists are effective in blocking PAR1-mediated migration in both established cell lines and primary patient lung carcinomas.

The PAR1 i3 Pepducin Inhibits Tumor Growth of Lung Carcinomas in Xenograft Models PAR1 expression level is correlated with reduced survival of patients with NSCLC. To define the relative importance of PAR1 in lung tumor progression, in vivo mouse models were used. Furthermore, because it had been identified that blockade of PAR1 signaling with i3 pepducins blocks multiple signaling pathways including calcium signaling and the ERK1/2 pathway, whereas i1 pepducin inhibits only migration and partially inhibits calcium, it was of interest to compare the in vivo efficacy of these pepducins. An A549 lung adenocarcinoma xenograft model in nude mice was used to evaluate monotherapy with P1pal-7, P1pal-10S, P1pal-i1-11, or the VEGF antagonist Avastin. For comparison, we also tested CXCR1/2 pepducins X1/2pal-i1 and X1/2pal-i3 that previously were shown to inhibit inflammation (Kaneider et al., Nat Med, 11 (2005), pp. 661-665) and CXCR1/2-driven angiogenesis in ovarian cancer (Agarwal et al., Cancer Res, 70 (2010), pp. 5880-5890).

It was found that the i3-derived P1pal-7 and Avastin gave comparable significant reductions (P <0.01) in tumor progression with 75% inhibition (FIGS. 13A-C). There was also a significant reduction (P <0.05) in tumor growth using the i3-derived P1pal-10S with 40% inhibition, but the i1-derived P1pal-i1-11 did not inhibit the long-term growth of the A549 tumors. Interestingly, the i1-derived P1pal-i1-11 was initially effective for the first 3 weeks and achieved significant blockade of tumor growth by day 20 (P<0.01). However, after this early protective stage, there was a rapid escape in tumor growth with the i1-derived pepducin. Tumor growth reduction with i3-derived pepducin treatments was accompanied by necrosis. The CXCR1/2-derived X1/2pal-i3 and X1/2pal-i1 pepducins had no apparent effect on tumor growth. These results suggest that monotherapy with i3-derived PAR1 pepducins may provide significant inhibition of lung carcinoma tumor growth in mice and identify PAR1 as a novel therapeutic target in lung cancer patients.

PAR1 has been shown to regulate VEGF production in several cell types (Huang et al., Thromb Haemost, 86 (2001), pp. 1094-1098) and VEGF is highly expressed in primary lung tumors (Ghio et al., 2006). Because the i3-based P1pal-7 pepducin had similar efficacy as Avastin in suppressing lung tumor growth of A549 xenografts, VEGF-A production was measured in the A549 tumor cells after 18 hours thrombin treatment. There was a significant two-fold mean increase in thrombin-dependent production of VEGF-A that could be completely blocked by the i3-based P1pal-7 and partially blocked with P1pal-10S (FIG. 13D). In contrast, the i1-based P1pal-i1-11 did not inhibit thrombin-dependent VEGF-A production. Notably, the ERIC inhibitor PD98059 also could suppress thrombin-mediated VEGF production. Unlike in ovarian cancer, no increase was found in PAR1-mediated IL-8 production in A549 cells, consistent with the observed lack of efficacy of CXCR1/2 pepducins in the A549 xenograft models. These xenograft data provide support for the role of a novel PAR1-ERK1/2-VEGF paracrine pathway that is an effective therapeutic target in the A549 adenocarcinoma lung cancer model.

Pharmacokinetics of PAR1 Pepducins

Pharmacokinetics of plasma levels of P1pal-7, P1pal-10S, and P1pal-i1-11 at 30 minutes, and at 1, 2, 4, 6, 8, and 16 hours was measured by LC/MS/MS to determine steady-state pepducin drug levels and the rate of elimination from mice. Subcutaneous injections of P1pal-7 (3 mg/kg or 10 mg/kg) into wild-type CF-1 mice (25 to 30 g) was followed by blood collection at various time points from the vena cava. As shown in FIG. 14A, the peak plasma level of P1pal-7 (10 mg/kg) reached 1.1 µmol/L, which persisted for 4 hours followed by elimination to 0.2 µmol/L at the 6-hour time point. Residual P1pal-7 levels were 10 nmol/L at the 16-hour time point. After the 4-hour plateau, the elimination rate was linear from 4 to 16 hours. The peak plasma level of 3 mg/kg P1pal-7 reached 0.6 µmol/L at 2 hours and elimination was linear between 2 hours and 16 hours. P1pal-10S (10 mg/kg) gave similar peak plasma level of 1.0 µmol/L as P1pal-7 (10 mg/kg) at 1 hour. However, there was rapid clearance after 1 hour. In contrast to P1pal-10S, P1pal-i1-11 (10 mg/kg) had a sustained plasma half-life with a peak plasma level of 5.0 mot L between 0.5 and 8 hours.

Lastly, the peak plasma level of P1pal-7 (10 mg/kg) was measured before and 1 hour after once-daily subcutaneous injection over 6 days to determine whether the peak plasma levels were consistent on daily administration. As shown in FIG. 14B, there was a relatively consistent peak plasma concentration of approximately 1 to 2 union P1pal-7, 1 hour after daily administration over 6 days. These results also indicate that after daily subcutaneous dosing, P1pal-7 does not accumulate in plasma in the mouse.

Emerging histopathologic evidence suggests that high expression of the G-protein-coupled PAR1 receptor is accompanied by an aggressive phenotype and poor outcome in patients with NSCLC (Ghio et al., 2006). In agreement with these clinicopathologic findings, data presented herein documented an increase in functional PAR1 protein, mRNA expression, and PAR1-dependent motility in a panel of NCI carcinomas and primary lung specimens as compared with normal lung epithelia. Silencing of PAR1 or pharmacologic blockade of PAR1 caused a significant decrease in motility of lung cancer cells. In contrast, the NCI lung adenocarcinomas and primary lung adenocarcinomas did not have increased levels of the related PAR2, PAR3, or PAR4 receptors.

By using pepducin technology directed against the intracellular loops of PAR1 divergent signaling pathways were delineated dependent on the i1 versus i3 loops in lung adenocarcinoma cell lines. Pepducins are lipidated peptides that are specifically targeted to the intracellular surface of their cognate GPCR, resulting in modulation of signal transduction. Pepducins targeting the PAR1 i3 loop completely inhibited cell motility, calcium mobilization, and ERK1/2 activation, while disruption of key amino acid residues in the loop identified as critical for G-protein interaction through 3D modeling reduced agonist capabilities. In contrast, the i1-targeted PAR1 pepducin inhibited cell motility, but did not have any effect on ERK1/2 activation and only partially suppressed calcium mobilization. These in vitro inhibitory data were highly concordant with the divergent pharmacologic effects of the i3 versus i1 pepducins observed in lung tumor models.

The i3- and i1-targeted PAR1 pepducins were further compared for efficacy in xenografts of A549 lung adenocarcinoma in nude mice. The i3-loop pepducins were efficacious as monotherapy in significantly blocking lung tumor growth whereas the ii pepducin was ineffective. From these in vitro and in vivo data, it was conclude that blockade of i3-loop functions including ERK1/2 activation and potentially calcium signaling may be more important than solely impacting cell motility as occurs with the i1-directed pepducin in lung adenocarcinoma models. In this regard, it previously was shown that PAR1 signals to ERK1/2 through both $G_i$ and $G_q$ proteins in rat astrocytes and that the $G_q$-ERK1/2 pathway is modulated by calcium. Because the i3-targeted pepducins were highly effective in blocking both PAR1-dependent calcium mobilization and ERK1/2 phosphorylation as compared with the i1-targeted pepducins, it is possible that the PAR1 i3 loop is more important for $G_q$ functions than the ii loop. Conversely, both the i1- and i3-targeted pepducins were equally effective in suppressing cell motility, which is largely dependent on $G_i$ signaling, providing evidence that both i1 and i3 are important for coupling to $G_i$.

The histopathology studies by Ghio et al., 2006, in 60 NSCLC patient samples also found that the majority (70%) of human lung tumors express the angiogenic factor VEGF and revealed a significant positive correlation between PAR-1 and VEGF expression (P<0.01). Interestingly, it was found here that the VEGF antibody, Avastin, had comparable efficacy as the PAR1 i3-loop pepducins in inhibiting human lung tumor growth in nude mice. As Avastin specifically blocks human VEGF but is ineffective against mouse-derived VEGF, the observed effects of Avastin were likely due to inhibition of the human lung adenocarcinoma-derived VEGF in the mouse xenografts. Indeed, we showed that PAR1 stimulates VEGF production through an ERK1/2-dependent pathway in the lung carcinoma cells. Moreover, PAR1 dependent production of VEGF was effectively blocked by the i3-loop pepducin but not by the i1-targeted pepducin, identifying PAR1-ERK1/2 signaling as a potentially important regulator of VEGF production in human lung carcinomas. These data are also consistent with the observed anti-angiogenic effects of the PAR1 i3 pepducin, P1pal-7, in xenograft models of invasive breast and ovarian tumors in mice (Boire et al., 2005; Agarwal et al., 2008).

In sum, data presented herein indicate that pharmaceutical compositions containing effective antagonistic pepducins targeting either i1 or i3 (preferably i3) can be used as treatment for cancers such as lung cancer.

Example III

Pharmaceutical Applications

Rationally designed antagonist pepducins of GPCRs may be administered to mammals in need of treatment, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The compounds or "agents" may be used in combination with one or more other known anti-thrombotic agents or pharmaceutical agents, including, e.g., a TP antagonist, a thromboxane antagonist, an ADP receptor antagonist, or a Factor Xa antagonist. When used in combination, it is understood that lower dosages of one or more of the combined anti-thrombotic agents may be utilized to achieve a desired effect, since the two or more anti-thrombotic agents may act additively or synergistically. Accordingly, a therapeutically effective dosage of one or more combined anti-thrombotic agents may correspond to less than 90%, less than 80%, less than 70%, less than 60%, less than 50%, less than 40%, less than 30% or less than 20% of the therapeutically effective dosage when the anti-thrombotic "agent" is administered alone. The two or more anti-thrombotic agents may be administered at the same time or at different times, by the same route of administration or by different routes of administration. For example, in order to regulate the dosage schedule, the anti-thrombotic agents may be administered separately in individual dosage units at the same time or different coordinated times. The respective substances can be individually formulated in separate unit dosage forms in a manner similar to that described above. However, fixed combinations of the anti-thrombotic agents are more convenient and are preferred, especially in tablet or capsule form for oral administration. Thus, the present invention also provides unit dose formulations comprising two or more anti-thrombotic agents, wherein each thrombotic "agent" is present in a therapeutically effective amount when administered in the combination.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending "agent" and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol. The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the prescribing physician will normally determine the daily dosage with the dosage generally varying according to the age, weight, and response of the individual patient, as well as the severity of the patient's symptoms. In an embodiment, a suitable amount of an "agent" is administered to a mammal undergoing treatment for thrombosis. Administration occurs in an amount of "agent" of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of agent. In another embodiment, the dosage comprises from about 1 mg to about 5000 mg of agent.

Example IV

Combination Therapy

One intended use of the herein described antagonists is the prophylactic treatment of patients at risk of a disease or condition hereby described as implicated by GPCR signaling pathways, such as lung cancer. Patients presenting with risk factors habitual smoking could be given a therapeutically effective dose of the agent according to a physician prescribed daily regimen. Patients would require close monitoring to ensure the treatment does not incur any undesirable side effects. Appropriate dosage would depend on the severity of any risk factors as well as age, gender of the patient and whether or not the patent has a family history of a thrombotic disease state or other genetic predisposition to a thrombotic disease state. In one embodiment, the herein described agent may be administered prophylacticly to a patient who is at an increased risk of thrombosis, for example, after surgery or after implantation of a medical device such as a stent or artificial organs, such as an artificial heart.

This application further contemplates the combination therapy of the herein described "agent" with one or more drugs that are known to treat one or more risk factors of thrombotic disease state.

In one embodiment, the drugs may be other known inhibitors of the underlying signaling pathway, condition or disease and combinations thereof.

In one example, combination therapy with the herein described "agent" may include other known anti-inflammatory agents and anti-cancer agents.

Example V

Other Therapeutic Applications

Antagonists against PAR-1 described herein may also find uses for the diagnosis and treatments of other medical conditions associated with PAR-1 activation. For example, medical conditions that may benefit from the compositions described herein, include, but not limited to, chronic intestinal inflammatory disorders, including inflammatory bowel disease (IBD), irritable bowel syndrome (IBS) and ulcerative colitis and fibrotic disorders, including liver fibrosis and lung fibrosis (see, for example, Vergnolle, et al., J Clin Invest (2004) 114(10): 1444; Yoshida, et al, Aliment Pharmacol Ther (2006) 24(Suppl 4):249; Mercer, et al., Ann NY Acad Sci (2007) 1096:86-88; Sokolova and Reiser, Pharmacol Ther (2007) PMID: 17532472), ischemia-reperfusion injury, including myocardial, renal, cerebral and intestinal ischemia-reperfusion injury (see, for example, Strande, et al., Basic Res. Cardiol (2007) 102(4):350-8; Sevastos, et al., Blood (2007) 109(2):577-583; Junge, et al., Proc Natl Acad Sci USA. (2003) 100(22): 13019-24 and Tsuboi, et al., Am J Physiol Gastrointest Liver Physiol (2007) 292(2):G678-83. Inhibiting PAR1 intracellular signaling can also be used to inhibit herpes simple virus (HSV1 and HSV2) infection of cells. See, Sutherland, et al., J Thromb Haemost (2007) 5(5):1055-61), in the pathogenesis of neurodegenerative diseases including Alzheimer's disease (AD) and Parkinson's disease (see Nishimura et al. Cell, Vol. 116, Issue 5, 671-682, (2004), Ishida et al. J Neuropathol Exp Neurol. 2006 January; 65(1):66-77; Rosenberg (2009) The Lancet Neurology, Vol. 8, 205-216, sepsis (Kaneider et al., Nature Immunology 8, 1303-1312 (2007)) or endometriosis (Hirota et al. J Clin Endocrinol Metab 2005; 90(6):3673-3679), cancer and angiogenesis (reviewed by Tsopanoglou N E and Maragoudakis M E. Semin Thromb Hemost. 2007 October, 33 (7):680-7).

The biology and pathophysiology of PAR activation in different tissues, cells, and species was recently reviewed by Steinhoff et al. Endocrine Reviews, February 2005, 26(1): 1-43.

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

Sequence listings and related materials in the ASCII text file named "2012-0628_TMC0462_Listing_ST25.txt" and created on Jun. 28, 2012 with a size of about 18 kilobytes, is hereby incorporated by reference.

We claim:

1. A chimeric polypeptide comprising:
   (a) a first domain comprising SEQ ID NO:20; and
   (b) a second domain, attached to said first domain, wherein said second domain comprises a naturally or non-naturally occurring hydrophobic moiety.

2. A pharmaceutical composition comprising:
   (a) a chimeric polypeptide comprising a first domain comprising SEQ ID NO:20 and a second domain, attached to said first domain, wherein said second domain comprises a naturally or non-naturally occurring hydrophobic moiety; and
   (b) a pharmaceutically-acceptable excipient, carrier, or diluent.

3. A chimeric polypeptide comprising:
   (a) a first domain that comprises a mutated full-length or fragment of SEQ ID NO:17, which is a portion of human protease-activated receptor 2 (PAR2), wherein said first domain comprises amino acids 274-284 of human PAR2 (amino acids 8-18 of SEQ ID NO:17), except that said first domain comprises a substitution of arginine (R) at position 284, and optionally an additional substitution at position 274; and
   (b) a second domain, attached to said first domain, wherein said second domain comprises a naturally or non-naturally occurring hydrophobic moiety;
   wherein said chimeric polypeptide is an effective PAR2 antagonist.

4. The chimeric polypeptide of claim 3, wherein said substitution of the arginine (R) at position 284 in a human PAR2 is a substitution with another residue having a shorter side chain.

5. The chimeric polypeptide of claim 4, wherein said residue having a shorter side chain is serine or glutamine.

6. The chimeric polypeptide of claim 3, wherein said first domain comprises a substitution at position 274.

7. The chimeric polypeptide of claim 3, wherein said first domain further comprises amino acid 285 of said human PAR2 (amino acid 19 of SEQ ID NO:17).

8. The chimeric polypeptide of claim 7, wherein said first domain further comprises amino acids 286 and 287 of said human PAR2 (amino acids 20 and 21 of SEQ ID NO:17), except that said first domain optionally comprises a substitution at position 287.

9. The chimeric polypeptide of claim 8, wherein said first domain comprises a substitution at position 287.

10. The chimeric polypeptide of claim 3, wherein said first domain further comprises amino acids 270 to 273 of said human PAR2 (amino acids 4-7 of SEQ ID NO:17).

11. The chimeric polypeptide of claim 10, wherein said first domain further comprises amino acids 267 to 269 of said human PAR2 (amino acids 1-3 of SEQ ID NO:17).

12. The chimeric polypeptide of claim 3, wherein said first domain comprises amino acids 267-287 of human protease-activated receptor-2 (PAR2), except that said first domain comprises a substitution of arginine (R) at position 284, and optionally an additional substitution at position 274.

* * * * *